United States Patent [19]
Chiu et al.

[11] Patent Number: 5,750,365
[45] Date of Patent: May 12, 1998

[54] ISOLATED NUCLEIC ACID ENCODING A NEWT ACIDIC FIBROBLAST GROWTH FACTOR (AFGF)

[75] Inventors: Ing Ming Chiu, Dublin; Matthew L. Poulin, Columbus, both of Ohio

[73] Assignee: The Ohio State University Research Foundation, Columbus, Ohio

[21] Appl. No.: 70,165

[22] Filed: May 28, 1993

[51] Int. Cl.$^6$ .................................................. C17K 15/19
[52] U.S. Cl. .................. 435/691; 435/252.3; 435/320.1; 435/69.4; 536/23.5
[58] Field of Search .......................... 536/23.5; 435/69.1, 435/69.4, 91.1, 91.4, 252.3, 252.33, 320.1; 530/399

[56] References Cited

U.S. PATENT DOCUMENTS 4,683,195  7/1987  Mullis et al. ............................... 435/6

OTHER PUBLICATIONS

Wozney, Methods in Enzymol 182:738–749 (1990).
Krust et al. EMBO J. 5:891–897 (1986).
Gospodarowicz Methods in Enzymol 147:106–119 (1987).
Basilico et al. Adv. Cancer Res. 59:115–165 (1992).
Gospodarowicz et al. Endocrine Rev 8:95–114 (1987).
Jimenez–Gallejo et al. Science 230:1385–1388 (1985).
Gautsehi–Sova et al. Biochem Biophys Res Comm 140:874–880 (1986).
Basilico et al., 1992, The FGF family of growth factors and oncogenes. Adv. Cancer Res. 59:115–165.
Jaye et al., 1986, Human endothelial cell growth factor: cloning, nucleotide sequence, and chromosomal localization. Science 23:541–545.
Wang et al., 1989, Cloning of the gene coding for human class I heparin–binding growth factor and its expression in fetal tissue. Mol. Cell. Biol. 9:2387–2395.
Abraham et al., 1986, Human basic fibroblast growth factor: nucleotide sequence and genomic organization. EMBO J. 5:2523–2528.
Dickson et al., 1987, Potential oncogene product related to growth factors. Nature 326–833.
Acland et al., 1990, Subcellular fate of int–2 oncoprotein is determined by choice of initiation codon. Nature 343:662–665.
Delli–Bovi et al., 1987, An oncogene isolated by transfection of Kaposi's sarcoma DNA encodes a growth factor that is a member of the FGF family, Cell 50:729–737.
Taira et al., 1987, cDNA sequence of human transforming gene hst and identification of the coding sequence required for transforming activity. Proc. Natl. Acad. Sci. USA 84:2980–2984.
Zhan et al., 1988, The human FGF–5 oncogene encodes a novel protein related to fibroblast growth factors. Mol. Cell. Biol. 8:3487–3495.
deLapeyriere et al., 1990, Structure, chromosome mapping, and expression of the murine FGF–6 gene. Oncogene 5:823–831.

Finch et al., 1989, Human KGF is FGF–related with properties of a paracrine effector of epithelial cell growth. Science 245:752–755.
Tanaka et al., 1992, Cloning and characterization of an androgen–induced growth factor essential for the androgen–dependent growth of mouse mammary carcinoma cells. Proc. Natl. Acad. Sci. USA 89:8928–8932.
Werner et al., 1992, Large induction of keratinocyte growth factor expression in the dermis during wound healing. Proc. Natl. Acad. Sci. USA 89:6896–6900.
Johnson et al., 1993, Structural and functional diversity in the FGF receptor multigene family, Adv. Cancer Res. 60:1–41.
Ruta et al., 1989, Receptor for acidic fibroblast growth factor is related to the tyrosine kinase encoded by the fms–like gene (FLG). Proc. Natl. Acad. Sci. USA 86:8722–8726.
Dionne et al., 1990, Cloning and expression of two distinct high–affinity receptors cross–reacting with acidic and basic fibroblast growth factor. EMBO J. 9:2685–2692.
Johnson et al., 1990, Diverse forms of a receptor for acidic and basic fibroblast growth factors. Mol. Cell. Biol. 10:4728–4736.
Kornbluth et al., 1988, Novel tyrosine kinase identified by phosphotyrosine antibody screening of cDNA libraries. Mol. Cell. Biol. 8:5541–5544.
Keegan et al., 1991, Isolation of an additional member of the fibroblast growth factor receptor family, FGFR–3. Proc. Natl. Acad. Sci. USA 88:1095–1099.
Partanen et al., 1991, FGFR–4, a novel acidic fibroblast growth factor receptor with a distinct expression pattern. EMBO J. 10:1347–1354.
Williams et al, 1988, The immunoglobulin superfamily–domains for cell surface recognition. Ann. Rev. Immunol. 6:381–405.
Mansukhani et al., 1990, A murine fibroblast growth factor (FGF) receptor expressed in CHO cells is activated by basic FGF and Kaposi FGF. Proc. Natl. Acad. Sci. USA 87:4378–4382.

(List continued on next page.)

Primary Examiner—John Ulm
Attorney, Agent, or Firm—Emch, Schaffer, Schaub & Porcello

[57] ABSTRACT

The present invention relates to novel newt aFGF cDNA and sequence, newt FGFR1 cDNA and sequence, newt FGFR2 cDNA and sequence, newt FGFR3 cDNA and sequence, newt KGFR cDNA and sequence, and CHO-KL cell line (KPTr2-2) expressing newt KGFR. Mutant cell lines (Tr31-5-1 and Tr33-1-2) that become non-responsive to aFGF stimulation are used to differentiate biological activities among different forms of aFGF and other FGF proteins. These novel sequences and cell lines substantially enhance the availability of newt acidic fibroblast growth factor and are useful for producing compositions for promoting growth and/or wound healing.

20 Claims, 14 Drawing Sheets

OTHER PUBLICATIONS

Fujita et al., 1991, The expression of two isoforms of the human fibroblast growth factor receptor (flg) is directed by alternative splicing. *Biochem. Biophys. Res. Comm.* 174:946–951.

Champion–Arnaud et al., 1991, Multiple mRNAs code for proteins related to the BEK fibroblast growth factor receptor. *Oncogene* 6:979–987.

Eisemann et al., 1991, Alternative splicing generates at least five different isoforms of the human basic–FGF receptor. *Oncogene* 6:1195–1202.

Johnson et al., 1991, The human fibroblast growth factor receptor genes: A common structural arrangement underlies the mechanisms for generating receptor forms that differ in their third immunoglobulin domain. *Mol. Cell. biol.* 11:4627–4634.

Yayon et al., 1992, A confined variable region confers ligand specificity on fibroblast growth factor receptors: Implications for the origin of the immunoglobulin fold. *EMBO J.* 11:1885–1890.

Miki et al., 1991, Expression cDNA cloning of the KGF receptor by creation of a transforming autocrine loop. *Science* 251:72–75.

Miki et al., 1992, Determination of ligand–binding specificity by alternative splicing: Two distinct growth factor receptors encoded by a single gene. *Proc. Natl. Acad. Sci. USA* 89:246–250.

Mansukhani et al., 1992, Characterization of the murine BEK fibroblast growth factor (FGF) receptor: Activation by three members of the FGF family and requirement for heparin. *Proc. Natl. Acad. Sci. USA* 89:3305–3309.

Whitman et al., 1989, Growth factors in early embryogenesis. *Annu. Rev. Cell Biol.* 5:93–117.

Hebert et al., 1990, Isolation of cDNAs encoding four mouse FGF family members and characterization of their expression patterns during embryogenesis. *Dev. Biol.* 138:454–463.

Niswander et al., 1992, FGF–4 expression during gastrulation, myogenesis, limb and tooth development in the mouse. *Development* 114:755–768.

Tannahill et al., 1992, Development expression of the Xenopus int–2(FGF–3) gene: Activation by mesodermal and neural induction. *Development* 115:696–702.

Mescher et al, 1979, Mitogenic effect of a growth factor derived from myelin on denervated regenerates of newt forelimbs. *J. Exp. Zool.* 207:497–503.

Gospodarowicz et al., 1980, Fibroblast growth factor and the control of vertebrate regeneration and repair. *Ann. N.Y. Acad. Sci.* 339:151–174.

Boilly et al., 1991, Acidic fibroblast growth factor is present in regenerating limb blastemas of axolotls and binds specifically to blastema tissue. *Dev. Biol.* 145:302–310.

Orr–Urtreger et al., 1991, Development expression of two murine fibroblast growth factor receptors, flg and bek. *Development* 113:1419–1434.

Peters et al., 1992, Two FGF receptor genes are differentially expressed in epithelial and mesenchymal tissues during limb formation and organogenesis in the mouse. *Development* 114:233–243.

Bunnag et al., 1991, Transformed phenotype conferred to NIH/3T3 cells by ectopic expression of heparin–binding growth factor 1/acidic fibroblast growth factor. *In Vitro Cell. Dev. Biol.* 27A:89–96.

Chiu et al., 1990, Alternative splicing generates two forms of mRNA coding for human heparin–binding growth factor 1. *Oncogene* 5:755–762.

```
GAATTCCCGACTGTTTCCCACGGAATAGGCTCTTGGATTAGCAGTATTTTCCCTTCCTACCAGTTTTGGGGGGTGTCGGTCGCCACCCCCACCTAGCTCTGGATAGAAGCACGTCCTGTA   120

CCTCGGCGCCCCAGAGCTGGGGGCCTGCGCCGGTCTTCGCCCCCCTGGCTCTCTCCACGCCAGGAGGTGGTGCACGCTTCAGAAGGTCTCTGATTTGTGGCGGTGAAGACCCTGGTTGC   240

AGCTCATGCTGGCGCAGAGGCCTTCTGATGGAAGAAGTCCACATGGCAGGCAGGACCGGGAGGTGGCATTGAGAGATGTTCAGCTGAGTTATCTTATGGGCCTGGTCATG           360
                                              MetGlyArgCysArgAlaGlyProGlyArgGlyIleGluMetPheSerTrpSerTyrLeuMetGly LeuValMet  12

GTTGCCACGGCAACACTTTCTCTAGCAAGGCCATCGTACAACATTGAGAAGATCAAACTGGAACCAGAAGATACTACAACAGGGATGATGAAGACGACGACGGCTGGAA            480
ValAlaThrAlaThrLeuSerLeuAlaArgProSerTyrAsnIleAlaGluAspTyrAsnIleAlaGluGluProGlyAspAspAlaAsnSerSerGlyAspAspAlaAsnAspGlySerGlu  52

GATTTCACAAATGACAACAACACATGAGGGCTCCGTACTGAGGACGAATACAGAGAAAAATTGGAAAAGAACTCCATGTGCCGCTGCCAACACTCGTGAAGTTCCGCTGTCCAGCCGGT   600
AspPheThrAsnAspAsnAsnThrGluGlyLeuValLeuLysLeuLysLeuGluLysLysLysLysLeuGluLysAsnSerMetCysArgCysGlnHisSerValLysPheArgCysProAlaGly  92

GGCAACCCTACGCCCTCCATGAGGTGGCTGAAGACGGAGTTCAAGGAGCACCGCATTGGGCTTCAAGGTACGTCAGTCAACACTTCAGCTGATCATGGAGAGCGTGGTT            720
GlyAsnProThrProSerMetArgTrpLeuLysThrGluPheLysGluHisArgIleGlyLeuGlnGlyThrSerValAsnThrSerAlaAspHisGlySerValVal                132

CCCTCTGACGAGGGCAACTACACCTGTATCATGGAGAACGAGTATGATCATCAATCACACCTGAATGTGTGCGAGGCGGCCAATACTCCAAGCTGGGCTT                      840
ProSerAspGluGlyAsnTyrThrCysIleMetGluAsnGluTyrGlyTyrSerIleAsnHisThrTyrSerAspAlaGlnHisProHisIleGluArgHisSerProIleGluGlnAlaGlyLeu  172

CCGGCAAACACGACCACAAAGTTGGGGTGATGCAGAGATTTGTCTGCAAAGTCTCAAAGTCTACAGTGACGCACAGCAGATCCTGAAGTTCTGACCTGCATAACGTGACTGAGGCGGAGC  960
ProAlaAsnThrThrLysValGlyValMetGlnArgPheValCysLysValTyrSerAspAlaGlnHisProHisIleGluArgHisPheGluLeuAsnGlySerLysIleGly            212

CCTGAGCGGGCATCCTATCTGAAAGTGCTAAAGGTGCTGAATTAATAGCTCCAATGCCGAAGTTCTGACCTGCATAACGTGACTGAGGCGGGACCAGTACACATGCAAAGTC          1080
ProAspHisGlyHisProTyrLeuLysProTyrLeuValLeuLysArgSerGlyIleAsnSerSerAsnAlaGluValAlaLeuThrLeuHisAsnValThrGluAlaAspAlaGlyIleGlnTyrThrCysLysVal  252

TCCAATTATATTGGGGAGGGCAACCAGCTCGCCTGCTCCACGGCTGCATCAGAGAAAGATGAAGAACGGAACTGGATTCATCATCGGAGTATACGGAAATCGCCATCTACTGT         1200
SerAsnTyrIleGlyGluGlyAsnGlnSerAlaTrpLeuThrValLeuProAlaSerGlyLeuLysAspSerSerGluTyrThrGlyLeuIleAlaIleTyrCys                     292

GTGGGAGGCTTCCTGATCACCTGACAATGGCACAATGGTGTCCATATGAAGGGCAGAGGCAAGAAGTCTGACTTGAGCGGGAAGGGCAAGCCTGTGCACAGCCCGTGCACAGCCCGTGCAGAGTCTC  1320
ValGlyValPheLeuIleThrCysMetIleGlyMetValCysHisMetLysGlyArgGlyLysGlyLysLysSerMetLysAsnPheSerProValAlaHisLysLeuSerLysLeu      332
```

NewtKGFR ArgSerGlyIleAsnSerSerAsn------AlaGluValLeuThrLeuHisAsnValThrGluAlaAspAla
          :::   ::                    ::::::            :::::::
Newtbek  AlaAlaGlyValAsnThrThrAspLysGluIleGluValLeuTyrValArgAsnValSerPheGluAspAla GlyGlnTyrThrCysLysValSerAsnTyrIleGlyGluAlaAsnGlnSerAlaTrpLeuThrValLeuProAlaSerGluLys
         :::                ::::::::::    ::                  ::::::::::::::::::
         GlyGluTyrThrCysLeuAlaGlyAsnSerThrGlyIleSerTyrHisThrAlaTrpLeuThrValPro

B

NewtKGFR ArgSerGlyIleAsnSerSerAsnAlaGluValLeuThrLeuHisAsnValThrGluAlaAspAlaGlyGln
          :::::::::::::::         :::                    :::::::::
HumanKGER HisSerGlyIleAsnSerSerAsnAlaGluValLeuAlaLeuPheAsnValThrGluAlaAspAlaGlyGlu TyrThrCysLysValSerAsnTyrIleGlyGluAlaAsnGlnSerAlaTrpLeuThrValProAlaSerGluLys
         :::          :::::::::::::    ::::::::::::::::::::::::::::::::::::
         TyrIleCysLysValSerAsnTyrIleGlyGlnAlaAsnGlnSerAlaTrpLeuThrValProLysProLysGlnGln

C

Newtbek  AlaAlaGlyValAsnThrThrAspLysGluIleGluValLeuTyrValArgAsnValSerPheGluAspAla
         ::::::::::::::::::::::::::::::::::::::    ::          ::::::::::
Humanbek AlaAlaGlyValAsnThrThrAspLysGluIleGluValLeuTyrIleArgAsnValThrPheGluAspAla GlyGluTyrThrCysLeuAlaGlyAsnSerThrGlyIleSerTyrHisThrAlaTrpLeuThrValPro
         ::::::::::::::::::::::::::        ::::::            :::::::::::::::
         GlyGluTyrThrCysLeuAlaGlyAsnSerIleGlySerPheHisSerAlaTrpLeuThrValPro

FIG. 3

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 261 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Notophthalmus viridescens
        ( D ) DEVELOPMENTAL STAGE: Adult
        ( F ) TISSUE TYPE: Brain ( v i i ) IMMEDIATE SOURCE:
        ( B ) CLONE: MP 75-1

( v i i i ) POSITION IN GENOME:
        ( C ) UNITS: bp ( i x ) FEATURE:
        ( A ) NAME/KEY: CDS
        ( B ) LOCATION: 1..261

( x ) PUBLICATION INFORMATION:
        ( A ) AUTHORS: Patrie, Kevin M
                     Botelho, Mary Jane
                     Ray, Subir K
                     Mehta, Veela B
                     Chiu, Ing- Ming
        ( C ) JOURNAL: J. Biol. Chem.
        ( K ) RELEVANT RESIDUES IN SEQ ID NO:1: FROM 1 TO 261

( x i ) SEQUENCE DESCRIPTION: SEQ ID NO:1:

```
CTT  CCC  AAT  GGA  AAC  TAC  CAG  AAG  CCT  AAG  CTC  CTG  TAC  TGC  AGC  AAC      4 8
Leu  Pro  Asn  Gly  Asn  Tyr  Gln  Lys  Pro  Lys  Leu  Leu  Tyr  Cys  Ser  Asn
 1              5                        10                       15

GGA  GGG  TAC  TTC  CTG  CGA  ATA  CTC  CCA  GAT  GGC  AAG  GTG  GAC  GGG  ACA      9 6
Gly  Gly  Tyr  Phe  Leu  Arg  Ile  Leu  Pro  Asp  Gly  Lys  Val  Asp  Gly  Thr
```

```
                    20                         25                         30
AGA  GAC  CGG  AGT  GAC  CCA  TAC  ATC  CAG  CTG  CAG  TTT  TAT  GCA  GAA  AGC    144
Arg  Asp  Arg  Ser  Asp  Pro  Tyr  Ile  Gln  Leu  Gln  Phe  Tyr  Ala  Glu  Ser
          35                        40                        45

GTG  GGC  GAG  GTA  TAC  ATC  AAG  AGT  CTG  GAG  ACA  GGC  CAG  TAC  TTG  GCG    192
Val  Gly  Glu  Val  Tyr  Ile  Lys  Ser  Leu  Glu  Thr  Gly  Gln  Tyr  Leu  Ala
     50                        55                        60

ATG  GAC  AGC  GAC  GGG  CAG  TTA  TAC  GCA  TCT  CAA  TCA  CCA  AGC  GAG  GAA    240
Met  Asp  Ser  Asp  Gly  Gln  Leu  Tyr  Ala  Ser  Gln  Ser  Pro  Ser  Glu  Glu
65                        70                        75                        80

TGC  CTG  TTC  TTG  GAG  CGA  CTG                                                 261
Cys  Leu  Phe  Leu  Glu  Arg  Leu
                    85
```

( 2 ) INFORMATION FOR SEQ ID NO:2:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu  Pro  Asn  Gly  Asn  Tyr  Gln  Lys  Pro  Lys  Leu  Leu  Tyr  Cys  Ser  Asn
1                        5                        10                       15

Gly  Gly  Tyr  Phe  Leu  Arg  Ile  Leu  Pro  Asp  Gly  Lys  Val  Asp  Gly  Thr
               20                        25                        30

Arg  Asp  Arg  Ser  Asp  Pro  Tyr  Ile  Gln  Leu  Gln  Phe  Tyr  Ala  Glu  Ser
          35                        40                        45

Val  Gly  Glu  Val  Tyr  Ile  Lys  Ser  Leu  Glu  Thr  Gly  Gln  Tyr  Leu  Ala
     50                        55                        60

Met  Asp  Ser  Asp  Gly  Gln  Leu  Tyr  Ala  Ser  Gln  Ser  Pro  Ser  Glu  Glu
65                        70                        75                        80

Cys  Leu  Phe  Leu  Glu  Arg  Leu
                    85
```

( 2 ) INFORMATION FOR SEQ ID NO:3:

( i ) SEQUENCE CHARACTERISTICS:
        ( A ) LENGTH: 1875 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Notophthalmus viridescens
        ( D ) DEVELOPMENTAL STAGE: Adult
        ( F ) TISSUE TYPE: Regenerating forelimb blastema
        ( G ) CELL TYPE: Mesenchyme and Epithelium ( v i i ) IMMEDIATE SOURCE:
        ( A ) LIBRARY: lambda gt11
        ( B ) CLONE: MP10-1

( v i i i ) POSITION IN GENOME:
        ( C ) UNITS: bp ( i x ) FEATURE:
        ( A ) NAME/KEY: CDS
        ( B ) LOCATION: 1..1164

(ix) FEATURE:
  (A) NAME/KEY: 3'UTR
  (B) LOCATION: 1165..1875

(x) PUBLICATION INFORMATION:
  (A) AUTHORS: Poulin, Matthew L
  (K) RELEVANT RESIDUES IN SEQ ID NO:3: FROM 1 TO 1874

(xi) SEQUENCE DESCRIPTION: SEQ ID NO:3:

```
GCC AGC TCT TCC ATG AGC TCT GGC GTT ATG CTG GTA CGG CCG TCG CGA        48
Ala Ser Ser Ser Met Ser Ser Gly Val Met Leu Val Arg Pro Ser Arg
 1           5                  10                  15

CTA TCG TCC AGT GGA AGC CCA ATG TTG ACT GGA GTC TCG GAG TAT GAA        96
Leu Ser Ser Ser Gly Ser Pro Met Leu Thr Gly Val Ser Glu Tyr Glu
             20                  25                  30

CTG CCA GAA GAT CCT CGC TGG GAG TTC TCA CGA GAC AGG TTA ATA TTG       144
Leu Pro Glu Asp Pro Arg Trp Glu Phe Ser Arg Asp Arg Leu Ile Leu
         35                  40                  45

GGC AAG CCT CTC GGA GAG GGC TGC TTT GGT CAG GTT GTA ATG GGA GAA       192
Gly Lys Pro Leu Gly Glu Gly Cys Phe Gly Gln Val Val Met Gly Glu
     50                  55                  60

GCA ATT GGC TTG GAC AAG GAG AAA CCC AAC CGA GTG ACT AAA GTA GCA       240
Ala Ile Gly Leu Asp Lys Glu Lys Pro Asn Arg Val Thr Lys Val Ala
 65                  70                  75                  80

GTG AAG ATG TTA AAA TCT GAC GCA ACT GAA AAG GAT TTG TCA GAT CTT       288
Val Lys Met Leu Lys Ser Asp Ala Thr Glu Lys Asp Leu Ser Asp Leu
                 85                  90                  95

ATT TCT GAG ATG GAA ATG ATG AAA ATG ATT GGA AAG CAC AAA AAC ATC       336
Ile Ser Glu Met Glu Met Met Lys Met Ile Gly Lys His Lys Asn Ile
            100                 105                 110

ATC AAT CTT CTT GGT GCA TGT ACG CAG GAT GGC CCA CTG TAT GTC ATT       384
Ile Asn Leu Leu Gly Ala Cys Thr Gln Asp Gly Pro Leu Tyr Val Ile
        115                 120                 125

GTG GAG TAC GCC TCA AAA GGT AAT CTG CGA GAA TAC TTG CGT GCC AGA       432
Val Glu Tyr Ala Ser Lys Gly Asn Leu Arg Glu Tyr Leu Arg Ala Arg
    130                 135                 140

CGT CCT CCG GGC ATG GAG TAC TGT TAT AAT CCC ATC CAT GCT TCC AAG       480
Arg Pro Pro Gly Met Glu Tyr Cys Tyr Asn Pro Ile His Ala Ser Lys
145                 150                 155                 160

GAC ATG CTG TCT TTT AAG GAC CTG GTG TCA TGT GCT TAC CAA GTA GCC       528
Asp Met Leu Ser Phe Lys Asp Leu Val Ser Cys Ala Tyr Gln Val Ala
                165                 170                 175

CGA GGA ATG GAG TAT CTT GCT TCT AAG AAG TGC ATC CAC CGT GAC CTT       576
Arg Gly Met Glu Tyr Leu Ala Ser Lys Lys Cys Ile His Arg Asp Leu
            180                 185                 190

GCA GCT CGA AAC GTG TTA GTA ACG GAA GAC AAT GTC ATG AAG ATT GCA       624
Ala Ala Arg Asn Val Leu Val Thr Glu Asp Asn Val Met Lys Ile Ala
        195                 200                 205

GAC TTT GGC TTG GCG CGA GAT ATC CAT CAC ATC GAT TAT TAC AAG AAG       672
Asp Phe Gly Leu Ala Arg Asp Ile His His Ile Asp Tyr Tyr Lys Lys
    210                 215                 220

ACG ACA AAT GGA CGA TTA CCG GTG AAG TGG ATG GCC CCT GAG GCA CTC       720
Thr Thr Asn Gly Arg Leu Pro Val Lys Trp Met Ala Pro Glu Ala Leu
225                 230                 235                 240

TTT GAC CGC ATA TAT ACT CAT CAA AGT GAC GTC TGG TCT TTC GGC GTG       768
Phe Asp Arg Ile Tyr Thr His Gln Ser Asp Val Trp Ser Phe Gly Val
                245                 250                 255

CTG CTG TGG GAG ATC TTC ACA CTG GGT GGC TCT CCT TAC CCT GGG GTG       816
Leu Leu Trp Glu Ile Phe Thr Leu Gly Gly Ser Pro Tyr Pro Gly Val
            260                 265                 270

CCA GTC GAA GAA CTC TTC AAG TTG TTA AAA GAG GGG CAC AGA ATG GAC       864
Pro Val Glu Glu Leu Phe Lys Leu Leu Lys Glu Gly His Arg Met Asp
```

|       |       |       |       | 275   |       |       |       |       | 280   |       |       |       |       | 285   |       |       |      |
|-------|-------|-------|-------|-------|-------|-------|-------|-------|-------|-------|-------|-------|-------|-------|-------|-------|------|
| AAA   | CCC   | GGC   | AAC   | TGC   | ACA   | AAT   | GAA   | CTA   | TAC   | ATG   | ATG   | ATG   | AGA   | GAC   | TGC   |       | 912  |
| Lys   | Pro   | Gly   | Asn   | Cys   | Thr   | Asn   | Glu   | Leu   | Tyr   | Met   | Met   | Met   | Arg   | Asp   | Cys   |       |      |
|       | 290   |       |       |       | 295   |       |       |       |       | 300   |       |       |       |       |       |       |      |
| TGG   | CAT   | GCA   | GTT   | CCA   | TCC   | CAA   | AGA   | CCA   | ACC   | TTC   | AAG   | CAG   | CTG   | GTT   | GAA   |       | 960  |
| Trp   | His   | Ala   | Val   | Pro   | Ser   | Gln   | Arg   | Pro   | Thr   | Phe   | Lys   | Gln   | Leu   | Val   | Glu   |       |      |
| 305   |       |       |       |       | 310   |       |       |       |       | 315   |       |       |       |       | 320   |       |      |
| GAT   | TTG   | GAC   | CGA   | ATT   | GTA   | GCA   | ATG   | ACC   | TCA   | AAT   | CAG   | GAA   | TAT   | TTG   | GAT   |       | 1008 |
| Asp   | Leu   | Asp   | Arg   | Ile   | Val   | Ala   | Met   | Thr   | Ser   | Asn   | Gln   | Glu   | Tyr   | Leu   | Asp   |       |      |
|       |       |       |       | 325   |       |       |       |       | 330   |       |       |       |       | 335   |       |       |      |
| CTG   | TCC   | ATG   | CCA   | ATG   | GAT   | CAG   | TAT   | TCT   | CCA   | GGT   | TTT   | CCA   | GAC   | ACA   | CGC   |       | 1056 |
| Leu   | Ser   | Met   | Pro   | Met   | Asp   | Gln   | Tyr   | Ser   | Pro   | Gly   | Phe   | Pro   | Asp   | Thr   | Arg   |       |      |
|       |       |       | 340   |       |       |       |       | 345   |       |       |       |       | 350   |       |       |       |      |
| AGT   | TCT   | ACG   | TGT   | TCC   | TCA   | GGA   | GAG   | GAC   | TCT   | GTG   | TTC   | TCC   | CAT   | GAT   | CCT   |       | 1104 |
| Ser   | Ser   | Thr   | Cys   | Ser   | Ser   | Gly   | Glu   | Asp   | Ser   | Val   | Phe   | Ser   | His   | Asp   | Pro   |       |      |
|       |       | 355   |       |       |       |       | 360   |       |       |       |       | 365   |       |       |       |       |      |
| TTT   | CCA   | GAT   | GAA   | CCT   | TGT   | CTT   | CCC   | AAG   | TAT   | CAA   | CAT   | GCC   | AAT   | GGT   | GGC   |       | 1152 |
| Phe   | Pro   | Asp   | Glu   | Pro   | Cys   | Leu   | Pro   | Lys   | Tyr   | Gln   | His   | Ala   | Asn   | Gly   | Gly   |       |      |
|       | 370   |       |       |       | 375   |       |       |       |       | 380   |       |       |       |       |       |       |      |
| CTT   | AAA   | AAA   | CGC   | TGACAGACAT |   | GACTTCCAGG |   | CAACAGAAAC |   | TGTGACCTCA |   |       |       |       |       |       | 1204 |
| Leu   | Lys   | Lys   | Arg   |       |       |       |       |       |       |       |       |       |       |       |       |       |      |
| 385   |       |       |       |       |       |       |       |       |       |       |       |       |       |       |       |       |      |

| TTTCTACCAT | CTAGCCTCTT | GGTTTTTATT | TTGGGAGGGC | AATGTTGTCC | AGCCATTAAA | 1264 |
|------------|------------|------------|------------|------------|------------|------|
| TTACCAGGAA | ATGTCTTATT | TTTTATTAT  | GGACCATAAC | ATGCGCCATT | ATAGCATCTC | 1324 |
| ACTAAGACCA | ACACCACCAG | CCCATGCAGC | ATGCCAGTTT | AACAAGCCTT | TATCTTGTAT | 1384 |
| CACATTGAGT | TATGTTTTTT | TTAACTTGAA | CATTTTACTT | ATATTTGGT  | CAATGTACTC | 1444 |
| GTCAAGTAGG | CAGACCATAA | AGTCCCTGGG | AACAGTCTGC | TATCTGGGAC | CTTGATAGGA | 1504 |
| AAAAGTGAAG | CAGTCTAACC | TCTGTGGCTT | CTTGAGATAC | ATTAAGACC  | AGAATGCCCT | 1564 |
| CCGGTACTTT | TCAAAAGAAA | TAAAGAACAG | TTGATCCATC | GCAACACAGA | GTACGAGAAA | 1624 |
| TACACACCTT | GGAGAATAAA | GGGATGCAGA | TAGTCTACCC | GCTTGCAGTT | CCATTCATGC | 1684 |
| TGAGAGCAGT | ATCTACTCAT | GGAAATTGGA | TGAGCCTATC | TGGGGAGTT  | CTAATGAGCC | 1744 |
| TGAACCCTCT | TTTGTTTTGG | ATTTTGGAAA | CTTGGATCAC | CCTTCAGTTC | TAGAAGGCCT | 1804 |
| CTTGGACACA | GCAACTTATG | ATTGGCTCTT | CTCTTAGGG  | ATGATTGAAG | CTTCCTTGCC | 1864 |
| AGTCGTTGTG | G          |            |            |            |            | 1875 |

( 2 ) INFORMATION FOR SEQ ID NO:4:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Ser | Ser | Ser | Met | Ser | Ser | Gly | Val | Met | Leu | Val | Arg | Pro | Ser | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ser | Ser | Ser | Gly | Ser | Pro | Met | Leu | Thr | Gly | Val | Ser | Glu | Tyr | Glu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Pro | Glu | Asp | Pro | Arg | Trp | Glu | Phe | Ser | Arg | Asp | Arg | Leu | Ile | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gly | Lys | Pro | Leu | Gly | Glu | Gly | Cys | Phe | Gly | Gln | Val | Val | Met | Gly | Glu |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ala | Ile | Gly | Leu | Asp | Lys | Glu | Lys | Pro | Asn | Arg | Val | Thr | Lys | Val | Ala |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| | | | | | | | | | | | | | | |
|---|---|---|---|---|---|---|---|---|---|---|---|---|---|---|
|Val|Lys|Met|Leu|Lys|Ser|Asp|Ala|Thr|Glu|Lys|Asp|Leu|Ser|Asp|Leu|
| | | |85| | | | |90| | | |95| | |

Val Lys Met Leu Lys Ser Asp Ala Thr Glu Lys Asp Leu Ser Asp Leu
                 85                      90                   95

Ile Ser Glu Met Glu Met Met Lys Met Ile Gly Lys His Lys Asn Ile
            100             105             110

Ile Asn Leu Leu Gly Ala Cys Thr Gln Asp Gly Pro Leu Tyr Val Ile
        115             120             125

Val Glu Tyr Ala Ser Lys Gly Asn Leu Arg Glu Tyr Leu Arg Ala Arg
130             135             140

Arg Pro Pro Gly Met Glu Tyr Cys Tyr Asn Pro Ile His Ala Ser Lys
145             150             155                         160

Asp Met Leu Ser Phe Lys Asp Leu Val Ser Cys Ala Tyr Gln Val Ala
                165             170                     175

Arg Gly Met Glu Tyr Leu Ala Ser Lys Lys Cys Ile His Arg Asp Leu
            180             185             190

Ala Ala Arg Asn Val Leu Val Thr Glu Asp Asn Val Met Lys Ile Ala
        195             200             205

Asp Phe Gly Leu Ala Arg Asp Ile His His Ile Asp Tyr Tyr Lys Lys
    210             215             220

Thr Thr Asn Gly Arg Leu Pro Val Lys Trp Met Ala Pro Glu Ala Leu
225             230             235                         240

Phe Asp Arg Ile Tyr Thr His Gln Ser Asp Val Trp Ser Phe Gly Val
                245             250             255

Leu Leu Trp Glu Ile Phe Thr Leu Gly Gly Ser Pro Tyr Pro Gly Val
            260             265             270

Pro Val Glu Glu Leu Phe Lys Leu Leu Lys Glu Gly His Arg Met Asp
        275             280             285

Lys Pro Gly Asn Cys Thr Asn Glu Leu Tyr Met Met Met Arg Asp Cys
    290             295             300

Trp His Ala Val Pro Ser Gln Arg Pro Thr Phe Lys Gln Leu Val Glu
305             310             315                         320

Asp Leu Asp Arg Ile Val Ala Met Thr Ser Asn Gln Glu Tyr Leu Asp
                325             330             335

Leu Ser Met Pro Met Asp Gln Tyr Ser Pro Gly Phe Pro Asp Thr Arg
            340             345             350

Ser Ser Thr Cys Ser Ser Gly Glu Asp Ser Val Phe Ser His Asp Pro
        355             360             365

Phe Pro Asp Glu Pro Cys Leu Pro Lys Tyr Gln His Ala Asn Gly Gly
    370             375             380

Leu Lys Lys Arg
385

( 2 ) INFORMATION FOR SEQ ID NO:5:

( i ) SEQUENCE CHARACTERISTICS:
        ( A ) LENGTH: 2675 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Notophthalmus viridescens
        ( D ) DEVELOPMENTAL STAGE: Adult
        ( F ) TISSUE TYPE: Regenerating forelimb blastema (G) CELL TYPE: Mesenchyme and Epithelium (vii) IMMEDIATE SOURCE:
    (A) LIBRARY: lambda gt11
    (B) CLONE: KP23-1

(viii) POSITION IN GENOME:
    (C) UNITS: bp (ix) FEATURE:
    (A) NAME/KEY: 5'UTR
    (B) LOCATION: 1..324

(ix) FEATURE:
    (A) NAME/KEY: CDS
    (B) LOCATION: 325..2511

(ix) FEATURE:
    (A) NAME/KEY: 3'UTR
    (B) LOCATION: 2512..2675

(x) PUBLICATION INFORMATION:
    (A) AUTHORS: Poulin, Matthew L
    (B) TITLE: Nucleotide sequences of two newt
        (Notophthalmus viridescens) fibroblast growth
        factor receptor-2 variants
    (C) JOURNAL: Biochim. Biophys. Acta
    (D) VOLUME: 1220
    (F) PAGES: 209-211
    (G) DATE: 1994
    (K) RELEVANT RESIDUES IN SEQ ID NO:5: FROM 1 TO 2675

(xi) SEQUENCE DESCRIPTION: SEQ ID NO:5:

```
GAATTCCCGA CTGTTTCCCA CGGAATAGGC TCTTGGATTA GCAGTATTTT CCCTTCCTAC      60

CAGTTTTGGG GGGTGTCGGT CGCACCCCCC ACCTAGCTCT GGATAGAAGC ACGTCCTGTA     120

CCTCGGCCGC CCCAGAGCTG GGGGCCTGCG CCGGTCTTCG CCCCCCTGGC TTCTCTCCAC     180

GCCAGAGGTG GTGCACGCTT CAGAAGGTCT CTGATTTGTG GCGGTGAAGA CCCTGGTTGC     240

AGCTCATGCT GGCGCAGAGG CCTTCTGATG GGAAGAAAGT CCACATGGCG ATGCAGGGCA     300

GGACCGGGGC GTGGCATTGA GAGG ATG TTC AGC TGG AGT TAT CTT ATG GGC      351
                          Met Phe Ser Trp Ser Tyr Leu Met Gly
                           1                5

CTG GTC ATG GTT GCC ACG GCA ACA CTT TCT CTA GCA AGG CCA TCG TAC      399
Leu Val Met Val Ala Thr Ala Thr Leu Ser Leu Ala Arg Pro Ser Tyr
 10              15              20                          25

AAC ATT GCA GAA GAT ACT ACA CTG GAA CCA GAA GAT GCA AAC TCA TCA      447
Asn Ile Ala Glu Asp Thr Thr Leu Glu Pro Glu Asp Ala Asn Ser Ser
                30              35              40

GGG GAT GAT GAA GAC GAC AAC GAC GGC TCG GAA GAT TTC ACA AAT GAC      495
Gly Asp Asp Glu Asp Asp Asn Asp Gly Ser Glu Asp Phe Thr Asn Asp
            45              50              55

AAC AAC CAC ATG AGG GCT CCG TAC TGG ACG AAT ACA GAA AAA TTG GAA      543
Asn Asn His Met Arg Ala Pro Tyr Trp Thr Asn Thr Glu Lys Leu Glu
        60              65              70

AAG AAA CTC CAT GCT GTG CCC GCT GCC AAC ACT GTG AAG TTC CGC TGT      591
Lys Lys Leu His Ala Val Pro Ala Ala Asn Thr Val Lys Phe Arg Cys
    75              80              85

CCA GCC GGT GGC AAC CCT ACG CCC TCC ATG AGG TGG CTG AAG AAC GGC      639
Pro Ala Gly Gly Asn Pro Thr Pro Ser Met Arg Trp Leu Lys Asn Gly
 90              95              100             105

AAG GAG TTC AAG CAG GAG CAC CGC ATT GGC GGC TTC AAG GTA CGT AGT      687
Lys Glu Phe Lys Gln Glu His Arg Ile Gly Gly Phe Lys Val Arg Ser
            110             115             120

CAA CAC TTC AGC CTG ATC ATG GAG AGC GTG GTT CCC TCT GAC GAG GGC      735
Gln His Phe Ser Leu Ile Met Glu Ser Val Val Pro Ser Asp Glu Gly
        125             130             135
```

| | | | | | | | | | | | | | | | | |
|---|---|---|---|---|---|---|---|---|---|---|---|---|---|---|---|---|
| AAC | TAC | ACC | TGT | ATC | ATG | GAG | AAC | GAG | TAT | GGA | TCC | ATC | AAT | CAC | ACC | 783 |
| Asn | Tyr | Thr | Cys | Ile | Met | Glu | Asn | Glu | Tyr | Gly | Ser | Ile | Asn | His | Thr | |
| | | 140 | | | | 145 | | | | | 150 | | | | | |
| TAC | CAC | CTG | GAT | GTT | GTC | GAG | CGG | TCA | CCC | CAC | CGG | CCA | ATA | CTC | CAA | 831 |
| Tyr | His | Leu | Asp | Val | Val | Glu | Arg | Ser | Pro | His | Arg | Pro | Ile | Leu | Gln | |
| | 155 | | | | | 160 | | | | | 165 | | | | | |
| GCT | GGG | CTT | CCG | GCA | AAC | ACA | ACC | ACA | AAA | GTT | GGG | GGC | GAT | GCA | GAG | 879 |
| Ala | Gly | Leu | Pro | Ala | Asn | Thr | Thr | Thr | Lys | Val | Gly | Gly | Asp | Ala | Glu | |
| 170 | | | | | 175 | | | | | 180 | | | | | 185 | |
| TTT | GTT | TGC | AAA | GTC | TAC | AGT | GAC | GCA | CAG | CCA | CAT | ATC | CAA | TGG | ATT | 927 |
| Phe | Val | Cys | Lys | Val | Tyr | Ser | Asp | Ala | Gln | Pro | His | Ile | Gln | Trp | Ile | |
| | | | | 190 | | | | | 195 | | | | | 200 | | |
| CGA | CAT | TTT | GAG | CTG | AAT | GGC | AGT | AAA | ATT | GGA | CCT | GAC | GGG | CAT | CCC | 975 |
| Arg | His | Phe | Glu | Leu | Asn | Gly | Ser | Lys | Ile | Gly | Pro | Asp | Gly | His | Pro | |
| | | | 205 | | | | | 210 | | | | | 215 | | | |
| TAT | CTG | AAA | GTG | CTA | AAG | GCG | GCC | GGT | GTT | AAC | ACC | ACG | GAC | AAA | GAG | 1023 |
| Tyr | Leu | Lys | Val | Leu | Lys | Ala | Ala | Gly | Val | Asn | Thr | Thr | Asp | Lys | Glu | |
| | | 220 | | | | | 225 | | | | | 230 | | | | |
| ATC | GAA | GTC | CTC | TAT | GTG | CGC | AAT | GTC | TCT | TTT | GAG | GAT | GCT | GGG | GAG | 1071 |
| Ile | Glu | Val | Leu | Tyr | Val | Arg | Asn | Val | Ser | Phe | Glu | Asp | Ala | Gly | Glu | |
| | 235 | | | | | 240 | | | | | 245 | | | | | |
| TAT | ACG | TGC | TTG | GCG | GGT | AAT | TCT | ACC | GGG | ATC | TCC | TAT | CAC | ACT | GCA | 1119 |
| Tyr | Thr | Cys | Leu | Ala | Gly | Asn | Ser | Thr | Gly | Ile | Ser | Tyr | His | Thr | Ala | |
| 250 | | | | | 255 | | | | | 260 | | | | | 265 | |
| TGG | TTG | ACC | GTT | CTG | CCA | GAT | GAA | GAA | CGG | GAA | CTG | GAT | TCA | TCA | TCG | 1167 |
| Trp | Leu | Thr | Val | Leu | Pro | Asp | Glu | Glu | Arg | Glu | Leu | Asp | Ser | Ser | Ser | |
| | | | | 270 | | | | | 275 | | | | | 280 | | |
| GAG | TAT | ACG | GAA | ATC | GCC | ATC | TAC | TGT | GTG | GGA | GGC | TTC | CTG | ATC | ACC | 1215 |
| Glu | Tyr | Thr | Glu | Ile | Ala | Ile | Tyr | Cys | Val | Gly | Gly | Phe | Leu | Ile | Thr | |
| | | 285 | | | | | 290 | | | | | 295 | | | | |
| TGC | ATG | ATT | GGC | ACA | ATC | ATG | GTG | TGC | CAC | ATG | AAG | GGC | AGA | GGC | AAG | 1263 |
| Cys | Met | Ile | Gly | Thr | Ile | Met | Val | Cys | His | Met | Lys | Gly | Arg | Gly | Lys | |
| | | 300 | | | | 305 | | | | | 310 | | | | | |
| AAG | TCT | GAC | TTC | AGC | AGC | CCA | CCC | GCT | GTG | CAC | AAG | CTG | AGC | AAG | AGT | 1311 |
| Lys | Ser | Asp | Phe | Ser | Ser | Pro | Pro | Ala | Val | His | Lys | Leu | Ser | Lys | Ser | |
| | 315 | | | | | 320 | | | | | 325 | | | | | |
| CTC | CCC | CTG | CGC | AGA | CAG | GTA | ACA | GTG | TCT | GCT | GAC | TCC | AGC | TCT | TCT | 1359 |
| Leu | Pro | Leu | Arg | Arg | Gln | Val | Thr | Val | Ser | Ala | Asp | Ser | Ser | Ser | Ser | |
| 330 | | | | | 335 | | | | | 340 | | | | | 345 | |
| ATG | AAC | TCC | AAC | ACT | CCA | CTG | GTC | CGG | ATC | ACC | ACT | CGC | CTG | TCT | TCC | 1407 |
| Met | Asn | Ser | Asn | Thr | Pro | Leu | Val | Arg | Ile | Thr | Thr | Arg | Leu | Ser | Ser | |
| | | | | 350 | | | | | 355 | | | | | 360 | | |
| AAC | AAT | GAC | ACC | CAC | TTG | CTG | GCC | GGG | GTC | TCC | GAG | TAT | GAG | CTG | CCA | 1455 |
| Asn | Asn | Asp | Thr | His | Leu | Leu | Ala | Gly | Val | Ser | Glu | Tyr | Glu | Leu | Pro | |
| | | | 365 | | | | | 370 | | | | | 375 | | | |
| GAG | GAC | CCC | AAG | TGG | GAG | TAT | CCA | AGG | GAA | AAG | CTC | ACG | CTG | GGG | AAG | 1503 |
| Glu | Asp | Pro | Lys | Trp | Glu | Tyr | Pro | Arg | Glu | Lys | Leu | Thr | Leu | Gly | Lys | |
| | | 380 | | | | | 385 | | | | | 390 | | | | |
| CCC | CTG | GGC | GAA | GGC | TGC | TTC | GGG | CAG | GTG | GTG | ATG | GCA | GAG | GCG | GTG | 1551 |
| Pro | Leu | Gly | Glu | Gly | Cys | Phe | Gly | Gln | Val | Val | Met | Ala | Glu | Ala | Val | |
| | 395 | | | | | 400 | | | | | 405 | | | | | |
| GGC | ATC | GAC | AAG | GAC | CGG | CCC | AAA | GAT | GCA | GCG | ACC | GTG | GCA | GTG | AAG | 1599 |
| Gly | Ile | Asp | Lys | Asp | Arg | Pro | Lys | Asp | Ala | Ala | Thr | Val | Ala | Val | Lys | |
| 410 | | | | | 415 | | | | | 420 | | | | | 425 | |
| ATG | CTG | AAA | GAC | GAT | GCA | ACC | GAG | AAG | GAT | CTT | TCT | GAT | CTG | GTG | TCT | 1647 |
| Met | Leu | Lys | Asp | Asp | Ala | Thr | Glu | Lys | Asp | Leu | Ser | Asp | Leu | Val | Ser | |
| | | | | 430 | | | | | 435 | | | | | 440 | | |
| GAG | ATG | GAA | ATG | ATG | AAG | ATG | ATT | GGG | AAG | CAT | AAA | AAT | ATC | ATC | AAT | 1695 |
| Glu | Met | Glu | Met | Met | Lys | Met | Ile | Gly | Lys | His | Lys | Asn | Ile | Ile | Asn | |
| | | 445 | | | | | 450 | | | | | 455 | | | | |

| | | | | | | | | | | | | | | | | |
|---|---|---|---|---|---|---|---|---|---|---|---|---|---|---|---|---|
| CTT | CTA | GGA | GCG | TGC | ACC | CAA | GAT | GGC | CCA | CTC | TAC | GTG | ATA | GTC | GAA | 1743 |
| Leu | Leu | Gly | Ala | Cys | Thr | Gln | Asp | Gly | Pro | Leu | Tyr | Val | Ile | Val | Glu | |
| | | 460 | | | | 465 | | | | | 470 | | | | | |
| TAT | GCC | TCC | AAG | GGG | AAC | TTG | CGT | GAA | TAC | TTG | CGC | ACC | CGC | CGC | CCA | 1791 |
| Tyr | Ala | Ser | Lys | Gly | Asn | Leu | Arg | Glu | Tyr | Leu | Arg | Thr | Arg | Arg | Pro | |
| | 475 | | | | 480 | | | | | 485 | | | | | | |
| CCT | GGC | ATG | GAG | TAC | TCC | TTT | GAC | ATC | AAC | AGA | ATT | CCT | GAA | GAG | CAG | 1839 |
| Pro | Gly | Met | Glu | Tyr | Ser | Phe | Asp | Ile | Asn | Arg | Ile | Pro | Glu | Glu | Gln | |
| 490 | | | | | 495 | | | | | 500 | | | | | 505 | |
| ATG | ACC | TTC | AAG | GAC | CTA | GTG | TCT | TGC | ACG | TAC | CAA | CTG | GCC | AGG | GGA | 1887 |
| Met | Thr | Phe | Lys | Asp | Leu | Val | Ser | Cys | Thr | Tyr | Gln | Leu | Ala | Arg | Gly | |
| | | | 510 | | | | | 515 | | | | | | 520 | | |
| ATG | GAG | TAC | CTG | GCA | TCA | CAG | AAG | TGC | ATC | CAT | CGG | GAC | TTG | GCA | GCT | 1935 |
| Met | Glu | Tyr | Leu | Ala | Ser | Gln | Lys | Cys | Ile | His | Arg | Asp | Leu | Ala | Ala | |
| | | | 525 | | | | 530 | | | | | | 535 | | | |
| CGG | AAT | GTC | TTG | GTG | ACG | GAA | ACC | AAC | GTC | ATG | AAA | ATT | GCA | GAT | TTT | 1983 |
| Arg | Asn | Val | Leu | Val | Thr | Glu | Thr | Asn | Val | Met | Lys | Ile | Ala | Asp | Phe | |
| | | 540 | | | | | 545 | | | | | 550 | | | | |
| GGT | TTG | GCC | CGA | GAC | ATC | AAC | AAC | ATC | GAC | TAC | TAC | AAA | AAA | ACA | ACC | 2031 |
| Gly | Leu | Ala | Arg | Asp | Ile | Asn | Asn | Ile | Asp | Tyr | Tyr | Lys | Lys | Thr | Thr | |
| | 555 | | | | | 560 | | | | | 565 | | | | | |
| AAT | GGC | CGG | CTC | CCC | GTG | AAG | TGG | ATG | GCT | CCC | GAG | GCG | CTG | TTT | GAC | 2079 |
| Asn | Gly | Arg | Leu | Pro | Val | Lys | Trp | Met | Ala | Pro | Glu | Ala | Leu | Phe | Asp | |
| 570 | | | | | 575 | | | | | 580 | | | | | 585 | |
| AGA | GTC | TAC | ACA | CAT | CAG | AGT | GAC | GTC | TGG | TCT | TTC | GGT | GTG | CTT | ATG | 2127 |
| Arg | Val | Tyr | Thr | His | Gln | Ser | Asp | Val | Trp | Ser | Phe | Gly | Val | Leu | Met | |
| | | | | 590 | | | | | 595 | | | | | 600 | | |
| TGG | GAG | ATC | TTC | ACA | CTG | GGG | GGT | TCC | CCA | TAC | CCT | GGA | ATT | CCA | GTT | 2175 |
| Trp | Glu | Ile | Phe | Thr | Leu | Gly | Gly | Ser | Pro | Tyr | Pro | Gly | Ile | Pro | Val | |
| | | | 605 | | | | | 610 | | | | | 615 | | | |
| GAA | GAA | CTT | TTC | AAG | CTC | CTT | AAG | GAA | GGC | CAC | CGA | ATG | GAC | AAG | CCT | 2223 |
| Glu | Glu | Leu | Phe | Lys | Leu | Leu | Lys | Glu | Gly | His | Arg | Met | Asp | Lys | Pro | |
| | | 620 | | | | | 625 | | | | | 630 | | | | |
| GGC | AAC | TGC | ACC | AAT | GAG | CTG | TAT | ACA | ATG | ATG | ACG | GAC | TGC | TGG | CGT | 2271 |
| Gly | Asn | Cys | Thr | Asn | Glu | Leu | Tyr | Thr | Met | Met | Thr | Asp | Cys | Trp | Arg | |
| | 635 | | | | | 640 | | | | | 645 | | | | | |
| GCT | GTG | CCC | TCG | CAA | AGA | CCC | ACT | TTC | AAG | CAG | CTT | GTT | GAG | GAT | CTA | 2319 |
| Ala | Val | Pro | Ser | Gln | Arg | Pro | Thr | Phe | Lys | Gln | Leu | Val | Glu | Asp | Leu | |
| 650 | | | | | 655 | | | | | 660 | | | | | 665 | |
| GAC | CGA | ATC | CTC | ACG | CAA | ACG | ACC | AAT | GAG | GAG | TAC | CTG | GAC | CTC | AAC | 2367 |
| Asp | Arg | Ile | Leu | Thr | Gln | Thr | Thr | Asn | Glu | Glu | Tyr | Leu | Asp | Leu | Asn | |
| | | | | 670 | | | | | 675 | | | | | 680 | | |
| AAC | CCT | CTG | GAG | CAG | TAC | TCG | CCG | AGC | TAT | CCG | GAT | ACC | AGG | AGT | TCC | 2415 |
| Asn | Pro | Leu | Glu | Gln | Tyr | Ser | Pro | Ser | Tyr | Pro | Asp | Thr | Arg | Ser | Ser | |
| | | | 685 | | | | | 690 | | | | | 695 | | | |
| TGC | TCT | TCT | GGG | GAT | GAC | TCT | GTC | TTC | TCC | CCG | GAC | GCA | ATG | CCC | TAC | 2463 |
| Cys | Ser | Ser | Gly | Asp | Asp | Ser | Val | Phe | Ser | Pro | Asp | Ala | Met | Pro | Tyr | |
| | | 700 | | | | | 705 | | | | | 710 | | | | |
| GAC | CCC | TGT | CTT | CCC | AAA | TCC | CAA | CAC | ACA | AAC | GGC | ACC | ATT | AAA | ACA | 2511 |
| Asp | Pro | Cys | Leu | Pro | Lys | Ser | Gln | His | Thr | Asn | Gly | Thr | Ile | Lys | Thr | |
| | 715 | | | | | 720 | | | | | 725 | | | | | |

TGAGGCCACA CAACCAGCAT AGACTCCCCG TTCCACCAAG AACTGTATAT ATATATATTT 2571

TTTTTTTAAG AAAAGTATAA AACAGCAGAA AACTAGCTTG GCACTTCTTA CTTCCTGCGG 2631

AGCCTCCAGC AGCCAGGGAG TGTGGGAGTC TCTGCCACGG ATCC 2675

( 2 ) INFORMATION FOR SEQ ID NO:6:

( i ) SEQUENCE CHARACTERISTICS:

( A ) LENGTH: 729 amino acids ( B ) TYPE: amino acid (D) TOPOLOGY: linear (ii) MOLECULE TYPE: protein (xi) SEQUENCE DESCRIPTION: SEQ ID NO:6:

```
Met Phe Ser Trp Ser Tyr Leu Met Gly Leu Val Met Val Ala Thr Ala
 1               5                  10                  15

Thr Leu Ser Leu Ala Arg Pro Ser Tyr Asn Ile Ala Glu Asp Thr Thr
            20                  25                  30

Leu Glu Pro Glu Asp Ala Asn Ser Ser Gly Asp Asp Glu Asp Asp Asn
        35                  40                  45

Asp Gly Ser Glu Asp Phe Thr Asn Asp Asn His Met Arg Ala Pro
    50                  55                  60

Tyr Trp Thr Asn Thr Glu Lys Leu Glu Lys Lys Leu His Ala Val Pro
 65                  70                  75                  80

Ala Ala Asn Thr Val Lys Phe Arg Cys Pro Ala Gly Gly Asn Pro Thr
                85                  90                  95

Pro Ser Met Arg Trp Leu Lys Asn Gly Lys Glu Phe Lys Gln Glu His
            100                 105                 110

Arg Ile Gly Gly Phe Lys Val Arg Ser Gln His Phe Ser Leu Ile Met
        115                 120                 125

Glu Ser Val Val Pro Ser Asp Glu Gly Asn Tyr Thr Cys Ile Met Glu
    130                 135                 140

Asn Glu Tyr Gly Ser Ile Asn His Thr Tyr His Leu Asp Val Val Glu
145                 150                 155                 160

Arg Ser Pro His Arg Pro Ile Leu Gln Ala Gly Leu Pro Ala Asn Thr
                165                 170                 175

Thr Thr Lys Val Gly Gly Asp Ala Glu Phe Val Cys Lys Val Tyr Ser
            180                 185                 190

Asp Ala Gln Pro His Ile Gln Trp Ile Arg His Phe Glu Leu Asn Gly
        195                 200                 205

Ser Lys Ile Gly Pro Asp Gly His Pro Tyr Leu Lys Val Leu Lys Ala
    210                 215                 220

Ala Gly Val Asn Thr Thr Asp Lys Glu Ile Glu Val Leu Tyr Val Arg
225                 230                 235                 240

Asn Val Ser Phe Glu Asp Ala Gly Glu Tyr Thr Cys Leu Ala Gly Asn
                245                 250                 255

Ser Thr Gly Ile Ser Tyr His Thr Ala Trp Leu Thr Val Leu Pro Asp
            260                 265                 270

Glu Glu Arg Glu Leu Asp Ser Ser Ser Glu Tyr Thr Glu Ile Ala Ile
        275                 280                 285

Tyr Cys Val Gly Gly Phe Leu Ile Thr Cys Met Ile Gly Thr Ile Met
    290                 295                 300

Val Cys His Met Lys Gly Arg Gly Lys Lys Ser Asp Phe Ser Ser Pro
305                 310                 315                 320

Pro Ala Val His Lys Leu Ser Lys Ser Leu Pro Leu Arg Arg Gln Val
                325                 330                 335

Thr Val Ser Ala Asp Ser Ser Ser Met Asn Ser Asn Thr Pro Leu
            340                 345                 350

Val Arg Ile Thr Thr Arg Leu Ser Ser Asn Asn Asp Thr His Leu Leu
        355                 360                 365

Ala Gly Val Ser Glu Tyr Glu Leu Pro Glu Asp Pro Lys Trp Glu Tyr
    370                 375                 380

Pro Arg Glu Lys Leu Thr Leu Gly Lys Pro Leu Gly Glu Gly Cys Phe
385                 390                 395                 400
```

```
Gly Gln Val Val Met Ala Glu Ala Val Gly Ile Asp Lys Asp Arg Pro
            405                 410                 415

Lys Asp Ala Ala Thr Val Ala Val Lys Met Leu Lys Asp Ala Thr
            420                 425                 430

Glu Lys Asp Leu Ser Asp Leu Val Ser Glu Met Glu Met Met Lys Met
            435                 440                 445

Ile Gly Lys His Lys Asn Ile Ile Asn Leu Leu Gly Ala Cys Thr Gln
            450                 455                 460

Asp Gly Pro Leu Tyr Val Ile Val Glu Tyr Ala Ser Lys Gly Asn Leu
465                 470                 475                 480

Arg Glu Tyr Leu Arg Thr Arg Arg Pro Pro Gly Met Glu Tyr Ser Phe
                485                 490                 495

Asp Ile Asn Arg Ile Pro Glu Glu Gln Met Thr Phe Lys Asp Leu Val
            500                 505                 510

Ser Cys Thr Tyr Gln Leu Ala Arg Gly Met Glu Tyr Leu Ala Ser Gln
            515                 520                 525

Lys Cys Ile His Arg Asp Leu Ala Ala Arg Asn Val Leu Val Thr Glu
            530                 535                 540

Thr Asn Val Met Lys Ile Ala Asp Phe Gly Leu Ala Arg Asp Ile Asn
545                 550                 555                 560

Asn Ile Asp Tyr Tyr Lys Lys Thr Thr Asn Gly Arg Leu Pro Val Lys
                565                 570                 575

Trp Met Ala Pro Glu Ala Leu Phe Asp Arg Val Tyr Thr His Gln Ser
            580                 585                 590

Asp Val Trp Ser Phe Gly Val Leu Met Trp Glu Ile Phe Thr Leu Gly
            595                 600                 605

Gly Ser Pro Tyr Pro Gly Ile Pro Val Glu Glu Leu Phe Lys Leu Leu
    610                 615                 620

Lys Glu Gly His Arg Met Asp Lys Pro Gly Asn Cys Thr Asn Glu Leu
625                 630                 635                 640

Tyr Thr Met Met Thr Asp Cys Trp Arg Ala Val Pro Ser Gln Arg Pro
                645                 650                 655

Thr Phe Lys Gln Leu Val Glu Asp Leu Asp Arg Ile Leu Thr Gln Thr
            660                 665                 670

Thr Asn Glu Glu Tyr Leu Asp Leu Asn Asn Pro Leu Glu Gln Tyr Ser
            675                 680                 685

Pro Ser Tyr Pro Asp Thr Arg Ser Ser Cys Ser Ser Gly Asp Asp Ser
    690                 695                 700

Val Phe Ser Pro Asp Ala Met Pro Tyr Asp Pro Cys Leu Pro Lys Ser
705                 710                 715                 720

Gln His Thr Asn Gly Thr Ile Lys Thr
                725
```

(2) INFORMATION FOR SEQ ID NO:7:

(i) SEQUENCE CHARACTERISTICS:
        (A) LENGTH: 1839 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:

(A) ORGANISM: Notophthalmus viridescens
(D) DEVELOPMENTAL STAGE: Adult
(F) TISSUE TYPE: Regenerating forelimb blastema
(G) CELL TYPE: Mesenchyme and Epithelium (vii) IMMEDIATE SOURCE:
    (A) LIBRARY: lambda gt11
    (B) CLONE: MJ3-1

(viii) POSITION IN GENOME:
    (C) UNITS: bp (ix) FEATURE:
    (A) NAME/KEY: CDS
    (B) LOCATION: 1..1134

(ix) FEATURE:
    (A) NAME/KEY: 3'UTR
    (B) LOCATION: 1135..1839

(x) PUBLICATION INFORMATION:
    (A) AUTHORS: Poulin, Matthew L
    (K) RELEVANT RESIDUES IN SEQ ID NO:7: FROM 1 TO 1839

(xi) SEQUENCE DESCRIPTION: SEQ ID NO:7:

```
AAC ACC CCT CTG GTC CGG ATC ACC CGC CTT TCA TCC AGC GAT GGG CCG      48
Asn Thr Pro Leu Val Arg Ile Thr Arg Leu Ser Ser Ser Asp Gly Pro
 1               5                  10                  15

ATG TTG GCC AAT GTG TCC GAG CTG GAG CTA CCC GCT GAT CCG AAA TGG      96
Met Leu Ala Asn Val Ser Glu Leu Glu Leu Pro Ala Asp Pro Lys Trp
             20                  25                  30

GAA TTG TCT CGT TCA CGC TTG ACT TTG GGC AAA CCT CTT GGG GAA GGA     144
Glu Leu Ser Arg Ser Arg Leu Thr Leu Gly Lys Pro Leu Gly Glu Gly
         35                  40                  45

TGC TTT GGC CAG GTG GTG ATG GTG GAT GCG GTT GGC ATT GAG AAG GAG     192
Cys Phe Gly Gln Val Val Met Val Asp Ala Val Gly Ile Glu Lys Glu
     50                  55                  60

AAG CCA AAT AAG GCC ACC ACA GTC GCT GTT AAG ATG TTG AAA GAT GAT     240
Lys Pro Asn Lys Ala Thr Thr Val Ala Val Lys Met Leu Lys Asp Asp
 65                  70                  75                  80

GCC ACC GAT AAA GAC CTG TCG GAC TTG GTC TCT GAG ATG GAA ATG ATG     288
Ala Thr Asp Lys Asp Leu Ser Asp Leu Val Ser Glu Met Glu Met Met
                 85                  90                  95

AAG ATG ATT GGG AAG CAC AAA AAC ATC ATT AAT CTC CTG GGA GCC TGC     336
Lys Met Ile Gly Lys His Lys Asn Ile Ile Asn Leu Leu Gly Ala Cys
             100                 105                 110

ACA CAG GAT GGC CCA CTC TAT GTG TTG GTG GAA TAT GCA TCC AAA GGA     384
Thr Gln Asp Gly Pro Leu Tyr Val Leu Val Glu Tyr Ala Ser Lys Gly
         115                 120                 125

AAC TTG CGG GAG TAC CTG AGG GCC CGA CGC CCT CCT GGC ATG GAT TAC     432
Asn Leu Arg Glu Tyr Leu Arg Ala Arg Arg Pro Pro Gly Met Asp Tyr
 130                 135                 140

TCC TTT GAC ACC TGC AAA CTT CCC GAA GAG CAG TTG ACC TTC AAG GAC     480
Ser Phe Asp Thr Cys Lys Leu Pro Glu Glu Gln Leu Thr Phe Lys Asp
145                 150                 155                 160

CTG GTG TCC TGT GCC TAT CAG GTG GCC CGC GGC ATG GAG TAC CTG GCC     528
Leu Val Ser Cys Ala Tyr Gln Val Ala Arg Gly Met Glu Tyr Leu Ala
                 165                 170                 175

TCT CAG AAG TGC ATA CAC CGA GAT CTG GCA GCC CGG AAC GTG CTA GTG     576
Ser Gln Lys Cys Ile His Arg Asp Leu Ala Ala Arg Asn Val Leu Val
             180                 185                 190

ACG GAT GAC AAC GTT ATG AAG ATT GCT GAT TTT GGC CTG GCA AGA GAT     624
Thr Asp Asp Asn Val Met Lys Ile Ala Asp Phe Gly Leu Ala Arg Asp
         195                 200                 205

GTG CAC AAC ATC GAC TAC TAC AAG AAA ACC ACA AAT GGT CGA CTG CCT     672
Val His Asn Ile Asp Tyr Tyr Lys Lys Thr Thr Asn Gly Arg Leu Pro
```

```
                    210                      215                      220
GTG  AAG  TGG  ATG  GCT  CCA  GAG  GCT  TTG  TTC  GAC  CGG  GTC  TAC  ACT  CAC     720
Val  Lys  Trp  Met  Ala  Pro  Glu  Ala  Leu  Phe  Asp  Arg  Val  Tyr  Thr  His
225                      230                      235                      240

CAA  AGC  GAT  GTA  TGG  TCG  TTT  GGA  GTG  CTT  CTG  TGG  GAG  ATC  TTC  ACG     768
Gln  Ser  Asp  Val  Trp  Ser  Phe  Gly  Val  Leu  Leu  Trp  Glu  Ile  Phe  Thr
                         245                      250                      255

CTG  GGA  GGC  TCA  CCG  TAC  CCT  GGA  ATC  CCG  GTG  GAA  GAA  CTC  TTT  AAG     816
Leu  Gly  Gly  Ser  Pro  Tyr  Pro  Gly  Ile  Pro  Val  Glu  Glu  Leu  Phe  Lys
                    260                      265                      270

CTG  TTA  AAA  GAA  GGG  CAT  CGA  ATG  GAC  AAG  CCA  GCA  AAC  TGC  ACG  CAT     864
Leu  Leu  Lys  Glu  Gly  His  Arg  Met  Asp  Lys  Pro  Ala  Asn  Cys  Thr  His
               275                      280                      285

GAG  CTG  TAT  ATG  ATC  ATG  CGA  GAG  TGT  TGG  CAT  GCA  GTG  CCA  TCC  CAG     912
Glu  Leu  Tyr  Met  Ile  Met  Arg  Glu  Cys  Trp  His  Ala  Val  Pro  Ser  Gln
     290                      295                      300

CGG  CCA  ACC  TTT  AAA  CAG  CTA  GTA  GAA  GAC  TTG  GAC  CGG  GTC  CTT  ACG     960
Arg  Pro  Thr  Phe  Lys  Gln  Leu  Val  Glu  Asp  Leu  Asp  Arg  Val  Leu  Thr
305                      310                      315                      320

GTG  ACA  TCC  ACT  GAT  GAG  TAC  CTC  GAC  CTC  TCT  GTG  CCC  TTT  GAG  CAG    1008
Val  Thr  Ser  Thr  Asp  Glu  Tyr  Leu  Asp  Leu  Ser  Val  Pro  Phe  Glu  Gln
                         325                      330                      335

TAT  TCG  CCA  GCA  TGC  CCA  GAC  AGC  CAC  AGC  AGC  TGC  TCT  TCT  GGG  GAC    1056
Tyr  Ser  Pro  Ala  Cys  Pro  Asp  Ser  His  Ser  Ser  Cys  Ser  Ser  Gly  Asp
                    340                      345                      350

GAT  TCG  GTC  TTT  ACA  CAC  GAC  CTG  CCC  GAG  GAG  CCC  TGC  CTT  CCC  AAG    1104
Asp  Ser  Val  Phe  Thr  His  Asp  Leu  Pro  Glu  Glu  Pro  Cys  Leu  Pro  Lys
               355                      360                      365

CAC  CAG  CAA  CAC  ATT  GGA  GGT  ACC  AGA  ACA  TGAGTGCTGA  AGGACAAAGA          1154
His  Gln  Gln  His  Ile  Gly  Gly  Thr  Arg  Thr
          370                      375

TCCAAACCAA  CCCAAGCATG  TAGGCTTCGA  GGCGCATGGA  CAGACCATCC  GGAAGGGCGG          1214

TTTCGCTGGA  CGGAGCCCAT  GAGTGAAAGA  AACCTTTTTT  TCTTTCTTTG  AGACGTAGGT          1274

TTTTTTACAT  GCTGTACAAG  AAGTCATGAA  GCACTGTTTG  CCTGAAGGA   CCTAATCTCT          1334

TGCCAAGATA  TAAATATATA  TGTGTGTCTG  TGTGTGTATA  TATATATATA  TTTTGAAAGC          1394

AGAATGTTTA  ATCTAGAGGT  ATGGACTTCT  TGACCTCTAG  TAATGTAATA  CAGTGTGCCA          1454

GAGTTGCCAA  TCTGTGCCTA  AGAATGCCAA  GAGGAGCAAA  GTTTAAAGAA  GAAAAAAACT          1514

ATAAAGGAAA  AAAGAAACTA  TAGTGAAGAA  TGTAAACCTG  TTAACTTTAT  GCAATCTGTG          1574

CATTAACCTT  TTTGGAGAAG  CCAAAAGGAA  CGTGGCCTAC  AAATGTTATG  CTTTTTCCAG          1634

TTGAGGTAGT  TTGGTACATT  TTCATTTTTT  TGTTGCCTTG  AACTGTTGTA  AGTTTTTTTC          1694

TATGGAAAAC  TTGGCCTTAA  AATTTCAGAA  CCCCCCCTAT  AATTTTGTCT  TTTGAGAGAG          1754

AAAGATTGCA  GTGGATTAAT  AGGCATGTTA  AAGTTGACAT  TTTCAAAGGT  GATTGAGGTA          1814

ATAGACAAAT  GAGGAACCGG  AATTC                                                   1839
```

( 2 ) INFORMATION FOR SEQ ID NO:8:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Asn  Thr  Pro  Leu  Val  Arg  Ile  Thr  Arg  Leu  Ser  Ser  Ser  Asp  Gly  Pro
 1              5                        10                       15
```

|     |     |     |     |     |     |     |     |     |     |     |     |     |     |
| --- | --- | --- | --- | --- | --- | --- | --- | --- | --- | --- | --- | --- | --- |
| Met | Leu | Ala | Asn<br>20 | Val | Ser | Glu | Leu<br>25 | Leu | Pro | Ala | Asp | Pro<br>30 | Lys | Trp |
| Glu | Leu | Ser<br>35 | Arg | Ser | Arg | Leu | Thr<br>40 | Leu | Gly | Lys | Pro | Leu<br>45 | Gly | Glu | Gly |
| Cys | Phe<br>50 | Gly | Gln | Val | Val | Met<br>55 | Val | Asp | Ala | Val | Gly<br>60 | Ile | Glu | Lys | Glu |
| Lys<br>65 | Pro | Asn | Lys | Ala | Thr<br>70 | Thr | Val | Ala | Val | Lys<br>75 | Met | Leu | Lys | Asp | Asp<br>80 |
| Ala | Thr | Asp | Lys | Asp<br>85 | Leu | Ser | Asp | Leu | Val<br>90 | Ser | Glu | Met | Glu | Met<br>95 | Met |
| Lys | Met | Ile | Gly<br>100 | Lys | His | Lys | Asn | Ile<br>105 | Ile | Asn | Leu | Leu | Gly<br>110 | Ala | Cys |
| Thr | Gln | Asp<br>115 | Gly | Pro | Leu | Tyr | Val<br>120 | Leu | Val | Glu | Tyr | Ala<br>125 | Ser | Lys | Gly |
| Asn | Leu<br>130 | Arg | Glu | Tyr | Leu | Arg<br>135 | Ala | Arg | Arg | Pro | Pro<br>140 | Gly | Met | Asp | Tyr |
| Ser<br>145 | Phe | Asp | Thr | Cys | Lys<br>150 | Leu | Pro | Glu | Glu | Gln<br>155 | Leu | Thr | Phe | Lys | Asp<br>160 |
| Leu | Val | Ser | Cys | Ala<br>165 | Tyr | Gln | Val | Ala | Arg<br>170 | Gly | Met | Glu | Tyr | Leu<br>175 | Ala |
| Ser | Gln | Lys | Cys<br>180 | Ile | His | Arg | Asp | Leu<br>185 | Ala | Ala | Arg | Asn | Val<br>190 | Leu | Val |
| Thr | Asp | Asp<br>195 | Asn | Val | Met | Lys | Ile<br>200 | Ala | Asp | Phe | Gly | Leu<br>205 | Ala | Arg | Asp |
| Val | His<br>210 | Asn | Ile | Asp | Tyr | Tyr<br>215 | Lys | Lys | Thr | Thr | Asn<br>220 | Gly | Arg | Leu | Pro |
| Val<br>225 | Lys | Trp | Met | Ala | Pro<br>230 | Glu | Ala | Leu | Phe | Asp<br>235 | Arg | Val | Tyr | Thr | His<br>240 |
| Gln | Ser | Asp | Val | Trp<br>245 | Ser | Phe | Gly | Val | Leu<br>250 | Leu | Trp | Glu | Ile | Phe<br>255 | Thr |
| Leu | Gly | Gly | Ser<br>260 | Pro | Tyr | Pro | Gly | Ile<br>265 | Pro | Val | Glu | Glu | Leu<br>270 | Phe | Lys |
| Leu | Leu | Lys<br>275 | Glu | Gly | His | Arg | Met<br>280 | Asp | Lys | Pro | Ala | Asn<br>285 | Cys | Thr | His |
| Glu | Leu<br>290 | Tyr | Met | Ile | Met | Arg<br>295 | Glu | Cys | Trp | His | Ala<br>300 | Val | Pro | Ser | Gln |
| Arg<br>305 | Pro | Thr | Phe | Lys | Gln<br>310 | Leu | Val | Glu | Asp | Leu<br>315 | Asp | Arg | Val | Leu | Thr<br>320 |
| Val | Thr | Ser | Thr | Asp<br>325 | Glu | Tyr | Leu | Asp | Leu<br>330 | Ser | Val | Pro | Phe | Glu<br>335 | Gln |
| Tyr | Ser | Pro | Ala<br>340 | Cys | Pro | Asp | Ser | His<br>345 | Ser | Ser | Cys | Ser | Ser<br>350 | Gly | Asp |
| Asp | Ser | Val<br>355 | Phe | Thr | His | Asp | Leu<br>360 | Pro | Glu | Glu | Pro | Cys<br>365 | Leu | Pro | Lys |
| His | Gln<br>370 | Gln | His | Ile | Gly | Gly<br>375 | Thr | Arg | Thr |

( 2 ) INFORMATION FOR SEQ ID NO:9:

( i ) SEQUENCE CHARACTERISTICS:
        ( A ) LENGTH: 2681 base pairs
        ( B ) TYPE: nucleic acid
        ( C ) STRANDEDNESS: double
        ( D ) TOPOLOGY: linear ( i i ) MOLECULE TYPE: cDNA (iii) HYPOTHETICAL: NO (iv) ANTI-SENSE: NO (vi) ORIGINAL SOURCE:
  (A) ORGANISM: Notophthalmus viridescens
  (D) DEVELOPMENTAL STAGE: Adult
  (F) TISSUE TYPE: Regenerating forelimb blastema
  (G) CELL TYPE: Mesenchyme and Epithelium (vii) IMMEDIATE SOURCE:
  (A) LIBRARY: lambda gt11
  (B) CLONE: KP19-1

(viii) POSITION IN GENOME:
  (C) UNITS: bp (ix) FEATURE:
  (A) NAME/KEY: 5'UTR
  (B) LOCATION: 1..324

(ix) FEATURE:
  (A) NAME/KEY: CDS
  (B) LOCATION: 325..2517

(ix) FEATURE:
  (A) NAME/KEY: 3'UTR
  (B) LOCATION: 2518..2681

(x) PUBLICATION INFORMATION:
  (A) AUTHORS: Poulin, Matthew L
       Chiu, Ing- Ming
  (B) TITLE: Nucleotide sequences of two newt
       (Notophthalmus viridescens) fibroblast growth
       factor receptor-2 variants
  (C) JOURNAL: Biochim. Biophys. Acta
  (D) VOLUME: 1220
  (F) PAGES: 209-211
  (G) DATE: 1994
  (K) RELEVANT RESIDUES IN SEQ ID NO:9: FROM 1 TO 2681

(xi) SEQUENCE DESCRIPTION: SEQ ID NO:9:

```
GAATTCCCGA CTGTTTCCCA CGGAATAGGC TCTTGGATTA GCAGTATTTT CCCTTCCTAC      60

CAGTTTTGGG GGGTGTCGGT CGCACCCCCC ACCTAGCTCT GGATAGAAGC ACGTCCTGTA     120

CCTCGGCCGC CCCAGAGCTG GGGGCCTGCG CCGGTCTTCG CCCCCCTGGC TTCTCTCCAC     180

GCCAGAGGTG GTGCACGCTT CAGAAGGTCT CTGATTTGTG GCGGTGAAGA CCCTGGTTGC     240

AGCTCATGCT GGCGCAGAGG CCTTCTGATG GGAAGAAAGT CCACATGGCG ATGCAGGGCA     300

GGACCGGGGC GTGGCATTGA GAGG ATG TTC AGC TGG AGT TAT CTT ATG GGC        351
                          Met Phe Ser Trp Ser Tyr Leu Met Gly
                           1               5

CTG GTC ATG GTT GCC ACG GCA ACA CTT TCT CTA GCA AGG CCA TCG TAC       399
Leu Val Met Val Ala Thr Ala Thr Leu Ser Leu Ala Arg Pro Ser Tyr
 10              15                  20                  25

AAC ATT GCA GAA GAT ACT ACA CTG GAA CCA GAA GAT GCA AAC TCA TCA       447
Asn Ile Ala Glu Asp Thr Thr Leu Glu Pro Glu Asp Ala Asn Ser Ser
                 30                  35                  40

GGG GAT GAT GAA GAC GAC AAC GAC GGC TCG GAA GAT TTC ACA AAT GAC       495
Gly Asp Asp Glu Asp Asp Asn Asp Gly Ser Glu Asp Phe Thr Asn Asp
                 45                  50                  55

AAC AAC CAC ATG AGG GCT CCG TAC TGG ACG AAT ACA GAA AAA TTG GAA       543
Asn Asn His Met Arg Ala Pro Tyr Trp Thr Asn Thr Glu Lys Leu Glu
             60                  65                  70

AAG AAA CTC CAT GCT GTG CCC GCT GCC AAC ACT GTG AAG TTC CGC TGT       591
Lys Lys Leu His Ala Val Pro Ala Ala Asn Thr Val Lys Phe Arg Cys
         75                  80                  85

CCA GCC GGT GGC AAC CCT ACG CCC TCC ATG AGG TGG CTG AAG AAC GGC       639
Pro Ala Gly Gly Asn Pro Thr Pro Ser Met Arg Trp Leu Lys Asn Gly
```

-continued

| | | | | | | | | | | | | | | | | |
|---|---|---|---|---|---|---|---|---|---|---|---|---|---|---|---|---|
| 90 | | | | 95 | | | | 100 | | | | 105 | | | | |
| AAG | GAG | TTC | AAG | CAG | GAG | CAC | CGC | ATT | GGC | GGC | TTC | AAG | GTA | CGT | AGT | 687 |
| Lys | Glu | Phe | Lys | Gln | Glu | His | Arg | Ile | Gly | Gly | Phe | Lys | Val | Arg | Ser | |
| | | | 110 | | | | | 115 | | | | | 120 | | | |
| CAA | CAC | TTC | AGC | CTG | ATC | ATG | GAG | AGC | GTG | GTT | CCC | TCT | GAC | GAG | GGC | 735 |
| Gln | His | Phe | Ser | Leu | Ile | Met | Glu | Ser | Val | Val | Pro | Ser | Asp | Glu | Gly | |
| | | | 125 | | | | | 130 | | | | | 135 | | | |
| AAC | TAC | ACC | TGT | ATC | ATG | GAG | AAC | GAG | TAT | GGA | TCC | ATC | AAT | CAC | ACC | 783 |
| Asn | Tyr | Thr | Cys | Ile | Met | Glu | Asn | Glu | Tyr | Gly | Ser | Ile | Asn | His | Thr | |
| | | 140 | | | | | 145 | | | | | 150 | | | | |
| TAC | CAC | CTG | GAT | GTT | GTC | GAG | CGG | TCA | CCC | CAC | CGG | CCA | ATA | CTC | CAA | 831 |
| Tyr | His | Leu | Asp | Val | Val | Glu | Arg | Ser | Pro | His | Arg | Pro | Ile | Leu | Gln | |
| | 155 | | | | | 160 | | | | | 165 | | | | | |
| GCT | GGG | CTT | CCG | GCA | AAC | ACA | ACC | ACA | AAA | GTT | GGG | GGC | GAT | GCA | GAG | 879 |
| Ala | Gly | Leu | Pro | Ala | Asn | Thr | Thr | Thr | Lys | Val | Gly | Gly | Asp | Ala | Glu | |
| 170 | | | | | 175 | | | | | 180 | | | | | 185 | |
| TTT | GTT | TGC | AAA | GTC | TAC | AGT | GAC | GCA | CAG | CCA | CAT | ATC | CAA | TGG | ATT | 927 |
| Phe | Val | Cys | Lys | Val | Tyr | Ser | Asp | Ala | Gln | Pro | His | Ile | Gln | Trp | Ile | |
| | | | | 190 | | | | | 195 | | | | | 200 | | |
| CGA | CAT | TTT | GAG | CTG | AAT | GGC | AGT | AAA | ATT | GGA | CCT | GAC | GGG | CAT | CCC | 975 |
| Arg | His | Phe | Glu | Leu | Asn | Gly | Ser | Lys | Ile | Gly | Pro | Asp | Gly | His | Pro | |
| | | | | 205 | | | | | 210 | | | | | 215 | | |
| TAT | CTG | AAA | GTG | CTA | AAG | CGC | TCT | GGA | ATT | AAT | AGC | TCC | AAT | GCC | GAA | 1023 |
| Tyr | Leu | Lys | Val | Leu | Lys | Arg | Ser | Gly | Ile | Asn | Ser | Ser | Asn | Ala | Glu | |
| | | 220 | | | | | 225 | | | | | 230 | | | | |
| GTT | CTG | ACC | CTG | CAT | AAC | GTG | ACT | GAG | GCG | GAC | CGG | GGC | CAG | TAC | ACA | 1071 |
| Val | Leu | Thr | Leu | His | Asn | Val | Thr | Glu | Ala | Asp | Arg | Gly | Gln | Tyr | Thr | |
| | 235 | | | | | 240 | | | | | 245 | | | | | |
| TGC | AAA | GTC | TCC | AAT | TAT | ATT | GGG | GAG | GCC | AAC | CAG | TCT | GCC | TGG | CTC | 1119 |
| Cys | Lys | Val | Ser | Asn | Tyr | Ile | Gly | Glu | Ala | Asn | Gln | Ser | Ala | Trp | Leu | |
| 250 | | | | | 255 | | | | | 260 | | | | | 265 | |
| ACG | GTG | CTG | CCT | GCA | TCA | GAG | AAA | GAT | GAA | GAA | CGG | GAA | CTG | GAT | TCA | 1167 |
| Thr | Val | Leu | Pro | Ala | Ser | Glu | Lys | Asp | Glu | Glu | Arg | Glu | Leu | Asp | Ser | |
| | | | 270 | | | | | 275 | | | | | 280 | | | |
| TCA | TCG | GAG | TAT | ACG | GAA | ATC | GCC | ATC | TAC | TGT | GTG | GGA | GGC | TTC | CTG | 1215 |
| Ser | Ser | Glu | Tyr | Thr | Glu | Ile | Ala | Ile | Tyr | Cys | Val | Gly | Gly | Phe | Leu | |
| | | | 285 | | | | | 290 | | | | | 295 | | | |
| ATC | ACC | TGC | ATG | ATT | GGC | ACA | ATC | ATG | GTG | TGC | CAC | ATG | AAG | GGC | AGA | 1263 |
| Ile | Thr | Cys | Met | Ile | Gly | Thr | Ile | Met | Val | Cys | His | Met | Lys | Gly | Arg | |
| | | | 300 | | | | | 305 | | | | | 310 | | | |
| GGC | AAG | AAG | TCT | GAC | TTC | AGC | AGC | CCA | CCC | GCT | GTG | CAC | AAG | CTG | AGC | 1311 |
| Gly | Lys | Lys | Ser | Asp | Phe | Ser | Ser | Pro | Pro | Ala | Val | His | Lys | Leu | Ser | |
| | 315 | | | | | 320 | | | | | 325 | | | | | |
| AAG | AGT | CTC | CCC | CTG | CGC | AGA | CAG | GTA | ACA | GTG | TCT | GCT | GAC | TCC | AGC | 1359 |
| Lys | Ser | Leu | Pro | Leu | Arg | Arg | Gln | Val | Thr | Val | Ser | Ala | Asp | Ser | Ser | |
| 330 | | | | | 335 | | | | | 340 | | | | | 345 | |
| TCT | TCT | ATG | AAC | TCC | AAC | ACT | CCA | CTG | GTC | CGG | ATC | ACC | ACT | CGC | CTG | 1407 |
| Ser | Ser | Met | Asn | Ser | Asn | Thr | Pro | Leu | Val | Arg | Ile | Thr | Thr | Arg | Leu | |
| | | | | 350 | | | | | 355 | | | | | 360 | | |
| TCT | TCC | AAC | AAT | GAC | ACC | CAC | TTG | CTG | GCC | GGG | GTC | TCC | GAG | TAT | GAG | 1455 |
| Ser | Ser | Asn | Asn | Asp | Thr | His | Leu | Leu | Ala | Gly | Val | Ser | Glu | Tyr | Glu | |
| | | | 365 | | | | | 370 | | | | | 375 | | | |
| CTG | CCA | GAG | GAC | CCC | AAG | TGG | GAG | TAT | CCA | AGG | GAA | AAG | CTC | ACG | CTG | 1503 |
| Leu | Pro | Glu | Asp | Pro | Lys | Trp | Glu | Tyr | Pro | Arg | Glu | Lys | Leu | Thr | Leu | |
| | | | 380 | | | | | 385 | | | | | 390 | | | |
| GGG | AAG | CCC | CTG | GGC | GAA | GGC | TGC | TTC | GGG | CAG | GTG | GTG | ATG | GCA | GAG | 1551 |
| Gly | Lys | Pro | Leu | Gly | Glu | Gly | Cys | Phe | Gly | Gln | Val | Val | Met | Ala | Glu | |
| | 395 | | | | | 400 | | | | | 405 | | | | | |
| GCG | GTG | GGC | ATC | GAC | AAG | GAC | CGG | CCC | AAA | GAT | GCA | GCG | ACC | GTG | GCA | 1599 |
| Ala | Val | Gly | Ile | Asp | Lys | Asp | Arg | Pro | Lys | Asp | Ala | Ala | Thr | Val | Ala | |

| | | | | | | | | | | | | | | | | |
|---|---|---|---|---|---|---|---|---|---|---|---|---|---|---|---|---|
| 410 | | | | | 415 | | | | | 420 | | | | | 425 | |
| GTG | AAG | ATG | CTG | AAA | GAC | GAT | GCA | ACC | GAG | AAG | GAT | CTT | TCT | GAT | CTG | 1647 |
| Val | Lys | Met | Leu | Lys | Asp | Asp | Ala | Thr | Glu | Lys | Asp | Leu | Ser | Asp | Leu | |
| | | | | 430 | | | | | 435 | | | | | 440 | | |
| GTG | TCT | GAG | ATG | GAA | ATG | ATG | AAG | ATG | ATT | GGG | AAG | CAT | AAA | AAT | ATC | 1695 |
| Val | Ser | Glu | Met | Glu | Met | Met | Lys | Met | Ile | Gly | Lys | His | Lys | Asn | Ile | |
| | | | | 445 | | | | | 450 | | | | | 455 | | |
| ATC | AAT | CTT | CTA | GGA | GCG | TGC | ACC | CAA | GAT | GGC | CCA | CTC | TAC | GTG | ATA | 1743 |
| Ile | Asn | Leu | Leu | Gly | Ala | Cys | Thr | Gln | Asp | Gly | Pro | Leu | Tyr | Val | Ile | |
| | | | | 460 | | | | | 465 | | | | | 470 | | |
| GTC | GAA | TAT | GCC | TCC | AAG | GGG | AAC | TTG | CGT | GAA | TAC | TTG | CGC | ACC | CGC | 1791 |
| Val | Glu | Tyr | Ala | Ser | Lys | Gly | Asn | Leu | Arg | Glu | Tyr | Leu | Arg | Thr | Arg | |
| | | | | 475 | | | | | 480 | | | | | 485 | | |
| CGC | CCA | CCT | GGC | ATG | GAG | TAC | TCC | TTT | GAC | ATC | AAC | AGA | ATT | CCT | GAA | 1839 |
| Arg | Pro | Pro | Gly | Met | Glu | Tyr | Ser | Phe | Asp | Ile | Asn | Arg | Ile | Pro | Glu | |
| 490 | | | | | 495 | | | | | 500 | | | | | 505 | |
| GAG | CAG | ATG | ACC | TTC | AAG | GAC | CTA | GTG | TCT | TGC | ACG | TAC | CAA | CTG | GCC | 1887 |
| Glu | Gln | Met | Thr | Phe | Lys | Asp | Leu | Val | Ser | Cys | Thr | Tyr | Gln | Leu | Ala | |
| | | | | 510 | | | | | 515 | | | | | 520 | | |
| AGG | GGA | ATG | GAG | TAC | CTG | GCA | TCA | CAG | AAG | TGC | ATC | CAT | CGG | GAC | TTG | 1935 |
| Arg | Gly | Met | Glu | Tyr | Leu | Ala | Ser | Gln | Lys | Cys | Ile | His | Arg | Asp | Leu | |
| | | | | 525 | | | | | 530 | | | | | 535 | | |
| GCA | GCT | CGG | AAT | GTC | TTG | GTG | ACG | GAA | ACC | AAC | GTC | ATG | AAA | ATT | GCA | 1983 |
| Ala | Ala | Arg | Asn | Val | Leu | Val | Thr | Glu | Thr | Asn | Val | Met | Lys | Ile | Ala | |
| | | | | 540 | | | | | 545 | | | | | 550 | | |
| GAT | TTT | GGT | TTG | GCC | CGA | GAC | ATC | AAC | AAC | ATC | GAC | TAC | TAC | AAA | AAA | 2031 |
| Asp | Phe | Gly | Leu | Ala | Arg | Asp | Ile | Asn | Asn | Ile | Asp | Tyr | Tyr | Lys | Lys | |
| | | | | 555 | | | | | 560 | | | | | 565 | | |
| ACA | ACC | AAT | GGC | CGG | CTC | CCC | GTG | AAG | TGG | ATG | GCT | CCC | GAG | GCG | CTG | 2079 |
| Thr | Thr | Asn | Gly | Arg | Leu | Pro | Val | Lys | Trp | Met | Ala | Pro | Glu | Ala | Leu | |
| 570 | | | | | 575 | | | | | 580 | | | | | 585 | |
| TTT | GAC | AGA | GTC | TAC | ACA | CAT | CAG | AGT | GAC | GTC | TGG | TCT | TTC | GGT | GTG | 2127 |
| Phe | Asp | Arg | Val | Tyr | Thr | His | Gln | Ser | Asp | Val | Trp | Ser | Phe | Gly | Val | |
| | | | | 590 | | | | | 595 | | | | | 600 | | |
| CTT | ATG | TGG | GAG | ATC | TTC | ACA | CTG | GGG | GGT | TCC | CCA | TAC | CCT | GGA | ATT | 2175 |
| Leu | Met | Trp | Glu | Ile | Phe | Thr | Leu | Gly | Gly | Ser | Pro | Tyr | Pro | Gly | Ile | |
| | | | | 605 | | | | | 610 | | | | | 615 | | |
| CCA | GTT | GAA | GAA | CTT | TTC | AAG | CTC | CTT | AAG | GAA | GGC | CAC | CGA | ATG | GAC | 2223 |
| Pro | Val | Glu | Glu | Leu | Phe | Lys | Leu | Leu | Lys | Glu | Gly | His | Arg | Met | Asp | |
| | | | 620 | | | | | 625 | | | | | 630 | | | |
| AAG | CCT | GGC | AAC | TGC | ACC | AAT | GAG | CTG | TAT | ACA | ATG | ATG | ACG | GAC | TGC | 2271 |
| Lys | Pro | Gly | Asn | Cys | Thr | Asn | Glu | Leu | Tyr | Thr | Met | Met | Thr | Asp | Cys | |
| | 635 | | | | | 640 | | | | | 645 | | | | | |
| TGG | CGT | GCT | GTG | CCC | TCG | CAA | AGA | CCC | ACT | TTC | AAG | CAG | CTT | GTT | GAG | 2319 |
| Trp | Arg | Ala | Val | Pro | Ser | Gln | Arg | Pro | Thr | Phe | Lys | Gln | Leu | Val | Glu | |
| 650 | | | | | 655 | | | | | 660 | | | | | 665 | |
| GAT | CTA | GAC | CGA | ATC | CTC | ACG | CAA | ACG | ACC | AAT | GAG | GAG | TAC | CTG | GAC | 2367 |
| Asp | Leu | Asp | Arg | Ile | Leu | Thr | Gln | Thr | Thr | Asn | Glu | Glu | Tyr | Leu | Asp | |
| | | | | 670 | | | | | 675 | | | | | 680 | | |
| CTC | AAC | AAC | CCT | CTG | GAG | CAG | TAC | TCG | CCG | AGC | TAT | CCG | GAT | ACC | AGG | 2415 |
| Leu | Asn | Asn | Pro | Leu | Glu | Gln | Tyr | Ser | Pro | Ser | Tyr | Pro | Asp | Thr | Arg | |
| | | | 685 | | | | | 690 | | | | | 695 | | | |
| AGT | TCC | TGC | TCT | TCT | GGG | GAT | GAC | TCT | GTC | TTC | TCC | CCG | GAC | GCA | ATG | 2463 |
| Ser | Ser | Cys | Ser | Ser | Gly | Asp | Asp | Ser | Val | Phe | Ser | Pro | Asp | Ala | Met | |
| | | 700 | | | | | 705 | | | | | 710 | | | | |
| CCC | TAC | GAC | CCC | TGT | CTT | CCC | AAA | TCC | CAA | CAC | ACA | AAC | GGC | ACC | ATT | 2511 |
| Pro | Tyr | Asp | Pro | Cys | Leu | Pro | Lys | Ser | Gln | His | Thr | Asn | Gly | Thr | Ile | |
| | 715 | | | | | 720 | | | | | 725 | | | | | |
| AAA | ACA | TGAGGCCACA | CAACCAGCAT | AGACTCCCCG | TTCCACCAAG | AACTGTATAT | | | | | | | | | | 2567 |
| Lys | Thr | | | | | | | | | | | | | | | |

-continued

```
730
ATATATATTT TTTTTTTAAG AAAAGTATAA AACAGCAGAA AACTAGCTTG GCACTTCTTA    2627
CTTCCTGCGG AGCCTCCAGC AGCCAGGGAG TGTGGGAGTC TCTGCCACGG ATCC          2681
```

( 2 ) INFORMATION FOR SEQ ID NO:10:

( i ) SEQUENCE CHARACTERISTICS:
        ( A ) LENGTH: 731 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Phe Ser Trp Ser Tyr Leu Met Gly Leu Val Met Val Ala Thr Ala
 1               5                  10                  15
Thr Leu Ser Leu Ala Arg Pro Ser Tyr Asn Ile Ala Glu Asp Thr Thr
             20                  25                  30
Leu Glu Pro Glu Asp Ala Asn Ser Gly Asp Asp Glu Asp Asp Asn
         35                  40                  45
Asp Gly Ser Glu Asp Phe Thr Asn Asp Asn His Met Arg Ala Pro
     50                  55                  60
Tyr Trp Thr Asn Thr Glu Lys Leu Glu Lys Lys Leu His Ala Val Pro
 65                  70                  75                  80
Ala Ala Asn Thr Val Lys Phe Arg Cys Pro Ala Gly Gly Asn Pro Thr
                 85                  90                  95
Pro Ser Met Arg Trp Leu Lys Asn Gly Lys Glu Phe Lys Gln Glu His
             100                 105                 110
Arg Ile Gly Gly Phe Lys Val Arg Ser Gln His Phe Ser Leu Ile Met
         115                 120                 125
Glu Ser Val Val Pro Ser Asp Glu Gly Asn Tyr Thr Cys Ile Met Glu
     130                 135                 140
Asn Glu Tyr Gly Ser Ile Asn His Thr Tyr His Leu Asp Val Val Glu
145                 150                 155                 160
Arg Ser Pro His Arg Pro Ile Leu Gln Ala Gly Leu Pro Ala Asn Thr
                 165                 170                 175
Thr Thr Lys Val Gly Gly Asp Ala Glu Phe Val Cys Lys Val Tyr Ser
             180                 185                 190
Asp Ala Gln Pro His Ile Gln Trp Ile Arg His Phe Glu Leu Asn Gly
         195                 200                 205
Ser Lys Ile Gly Pro Asp Gly His Pro Tyr Leu Lys Val Leu Lys Arg
     210                 215                 220
Ser Gly Ile Asn Ser Ser Asn Ala Glu Val Leu Thr Leu His Asn Val
225                 230                 235                 240
Thr Glu Ala Asp Arg Gly Gln Tyr Thr Cys Lys Val Ser Asn Tyr Ile
                 245                 250                 255
Gly Glu Ala Asn Gln Ser Ala Trp Leu Thr Val Leu Pro Ala Ser Glu
             260                 265                 270
Lys Asp Glu Glu Arg Glu Leu Asp Ser Ser Ser Glu Tyr Thr Glu Ile
         275                 280                 285
Ala Ile Tyr Cys Val Gly Gly Phe Leu Ile Thr Cys Met Ile Gly Thr
     290                 295                 300
Ile Met Val Cys His Met Lys Gly Arg Gly Lys Lys Ser Asp Phe Ser
305                 310                 315                 320
Ser Pro Pro Ala Val His Lys Leu Ser Lys Ser Leu Pro Leu Arg Arg
                 325                 330                 335
```

```
Gln Val Thr Val Ser Ala Asp Ser Ser Ser Met Asn Ser Asn Thr
            340                 345             350

Pro Leu Val Arg Ile Thr Thr Arg Leu Ser Ser Asn Asn Asp Thr His
        355                 360             365

Leu Leu Ala Gly Val Ser Glu Tyr Glu Leu Pro Glu Asp Pro Lys Trp
    370                 375             380

Glu Tyr Pro Arg Glu Lys Leu Thr Leu Gly Lys Pro Leu Gly Glu Gly
385                 390             395                     400

Cys Phe Gly Gln Val Val Met Ala Glu Ala Val Gly Ile Asp Lys Asp
                405             410                 415

Arg Pro Lys Asp Ala Ala Thr Val Ala Val Lys Met Leu Lys Asp Asp
            420             425             430

Ala Thr Glu Lys Asp Leu Ser Asp Leu Val Ser Glu Met Glu Met Met
            435             440             445

Lys Met Ile Gly Lys His Lys Asn Ile Ile Asn Leu Leu Gly Ala Cys
    450             455             460

Thr Gln Asp Gly Pro Leu Tyr Val Ile Val Glu Tyr Ala Ser Lys Gly
465             470             475                     480

Asn Leu Arg Glu Tyr Leu Arg Thr Arg Arg Pro Pro Gly Met Glu Tyr
                485             490             495

Ser Phe Asp Ile Asn Arg Ile Pro Glu Glu Gln Met Thr Phe Lys Asp
            500             505             510

Leu Val Ser Cys Thr Tyr Gln Leu Ala Arg Gly Met Glu Tyr Leu Ala
        515             520             525

Ser Gln Lys Cys Ile His Arg Asp Leu Ala Ala Arg Asn Val Leu Val
    530             535             540

Thr Glu Thr Asn Val Met Lys Ile Ala Asp Phe Gly Leu Ala Arg Asp
545             550             555                     560

Ile Asn Asn Ile Asp Tyr Tyr Lys Lys Thr Thr Asn Gly Arg Leu Pro
            565             570             575

Val Lys Trp Met Ala Pro Glu Ala Leu Phe Asp Arg Val Tyr Thr His
            580             585             590

Gln Ser Asp Val Trp Ser Phe Gly Val Leu Met Trp Glu Ile Phe Thr
        595             600             605

Leu Gly Gly Ser Pro Tyr Pro Gly Ile Pro Val Glu Glu Leu Phe Lys
    610             615             620

Leu Leu Lys Glu Gly His Arg Met Asp Lys Pro Gly Asn Cys Thr Asn
625             630             635                     640

Glu Leu Tyr Thr Met Met Thr Asp Cys Trp Arg Ala Val Pro Ser Gln
            645             650             655

Arg Pro Thr Phe Lys Gln Leu Val Glu Asp Leu Asp Arg Ile Leu Thr
            660             665             670

Gln Thr Thr Asn Glu Glu Tyr Leu Asp Leu Asn Asn Pro Leu Glu Gln
        675             680             685

Tyr Ser Pro Ser Tyr Pro Asp Thr Arg Ser Ser Cys Ser Ser Gly Asp
    690             695             700

Asp Ser Val Phe Ser Pro Asp Ala Met Pro Tyr Asp Pro Cys Leu Pro
705             710             715                     720

Lys Ser Gln His Thr Asn Gly Thr Ile Lys Thr
            725             730
```

( 2 ) INFORMATION FOR SEQ ID NO:11:

( i ) SEQUENCE CHARACTERISTICS:

(A) LENGTH: 26 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Notophthalmus viridescens (vii) IMMEDIATE SOURCE:
(B) CLONE: Oligonucleotide HBGF 306

(viii) POSITION IN GENOME:
(C) UNITS: bp (ix) FEATURE:
(A) NAME/KEY: CDS
(B) LOCATION: 1..26

(x) PUBLICATION INFORMATION:
(A) AUTHORS: Patrie, Kevin M
Botelho, Mary Jane
Ray, Subir K
Mehta, Veela B
Chiu, Ing- Ming
(C) JOURNAL: J. Biol. Chem.
(K) RELEVANT RESIDUES IN SEQ ID NO:11: FROM 1 TO 26

(xi) SEQUENCE DESCRIPTION: SEQ ID NO:11:

TTYACAGCNC TGACNGARAA RTTYAA    26

(2) INFORMATION FOR SEQ ID NO:12:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Notophthalmus viridescens (vii) IMMEDIATE SOURCE:
(B) CLONE: Oligonucleotide HBGF 603

(viii) POSITION IN GENOME:
(C) UNITS: bp (ix) FEATURE:
(A) NAME/KEY: CDS
(B) LOCATION: complement (1..23)

(x) PUBLICATION INFORMATION:
(A) AUTHORS: Patrie, Kevin M
Botelho, Mary Jane
Ray, Subir K
Mehta, Veela B
Chiu, Ing- Ming
(C) JOURNAL: J. Biol. Chem.
(K) RELEVANT RESIDUES IN SEQ ID NO:12: FROM 1 TO 23

(xi) SEQUENCE DESCRIPTION: SEQ ID NO:12:

TAGGTRTTRT ARTGRTTYTC YTC    23

ISOLATED NUCLEIC ACID ENCODING A NEWT ACIDIC FIBROBLAST GROWTH FACTOR (AFGF)

TECHNICAL FIELD

The present invention relates to recombinant DNA-directed synthesis of certain proteins, the recombinant DNA sequences themselves and cell lines which express the recombinant DNA and proteins. More particularly, the present invention relates to newt fibroblast growth factor CDNA and sequence and to fibroblast growth factor receptors, FGFR1, FGFR2, FGFR3 and KGFR which have been cloned from a newt (*Notophthalamus viridescens*) limb blastema cDNA library. The FGFR1 and FGFR2 have distinct roles in limb regeneration, despite their sharing a number of the FGF ligands.

The present invention was supported in part by grants from the NIH (RO1 CA45611, K04 CA01369, and P30 CA16058) who may have certain rights in the invention.

BACKGROUND OF THE INVENTION

The fibroblast growth factor (FGF) family contains eight members (Basilico et al., 1992, The FGF family of growth factors and oncogenes. *Adv. Cancer Res.* 59:115–165). This reference and all references cited herein are expressly incorporated herein by reference. The two prototypic members, acidic FGF (Jaye et al., 1986, Human endothelial cell growth factor: cloning, nucleotide sequence, and chromosomal localization. *Science* 23:541–545; Wang et al., 1989, Cloning of the gene coding for human class I heparin-binding growth factor and its expression in fetal tissue. *Mol. Cell. Biol.* 9:2387–2395) and basic FGF (Abraham et al., 1986, Human basic fibroblast growth factor: nucleotide sequence and genomic organization. *EMBO J.* 5:2523–2528) have no signal peptide but the remaining six members, FGF-3 (Dickson et al., 1987, Potential oncogene product related to growth factors. *Nature* 326–833; Acland et al., 1990, Sub-cellular fate of int-2 oncoprotein is determined by choice of initiation codon. *Nature* 343:662–665), FGF-4 (Delli-Bovi et al., 1987, An oncogene isolated by transfection of Kaposi's sarcoma DNA encodes a growth factor that is a member of the FGF family. *Cell* 50:729–737; Taira et al., 1987, cDNA sequence of human transforming gene hst and identification of the coding sequence required for transforming activity. *Proc. Natl. Acad. Sc. USA* 84:2980–2984), FGF-5 (Zhan et al., 1988, The human FGF-5 oncogene encodes a novel protein related to fibroblast growth factors. *Mol. Cell. Biol.* 8:3487–3495), FGF-6 (deLapeyriere et al., 1990, Structure, chromosome mapping, and expression of the murine FGF-6 gene. *Oncogene* 5:823–831), keratinocyte growth factor (KGF) (Finch et al., 1989, Human KGF is FGF-related with properties of a paracrine effector of epithelial cell growth. *Science* 245:752–755) and androgen-induced growth factor (AIGF) (Tanaka et al., 1992, Cloning and characterization of an androgen-induced growth factor essential for the androgen-dependent growth of mouse mammary carcinoma cells. *Proc. Natl. Acad. Sc. USA* 89:8928–8932) all have signal peptides. Various members of the FGF family are involved in cell growth, differentiation, and survival as well as embryonic induction and angiogenesis (Basilico et al., supra). Because the release of aFGF and bFGF is thought to be through dead or dying cells, it is implied that they are also involved in tissue repair. Moreover, KGF mRNA has been shown to be induced more than 160 fold during wound healing (Werner et al., 1992, Large induction of keratinocyte growth factor expression in the dermis during wound healing. *Proc. Natl. Acad. Sci. USA* 89:6896–6900).

As with most polypeptide growth factors, the FGF signal is transduced via membrane-spanning protein tyrosine kinase (PTK) receptors (Johnson et al., 1993, Structural and functional diversity in the FGF receptor multigene family, *Adv. Cancer Res.* 60:1–41). The four members of the FGF receptor family, flg/FGFR1 (Ruta et al., 1989, Receptor for acidic fibroblast growth factor is related to the tyrosine kinase encoded by the fms-like gene (FLG). *Proc. Natl. Acad. Sci. USA* 86:8722–8726; Dionne et al., 1990, Cloning and expression of two distinct high-affinity receptors cross-reacting with acidic and basic fibroblast growth factor. *EMBO J.* 9:2685–2692; Johnson et al., 1990, Diverse forms of a receptor for acidic and basic fibroblast growth factors. *Mol. Cell. Biol.* 10:4728–4736), bek/FGFR2 (Kornbluth et al., 1988, Novel tyrosine kinase identified by phosphotyrosine antibody screening of cDNA libraries. *Mol. Cell. Biol.* 8:5541–5544; Dionne et al., 1990, supra), FGFR3 (Keegan et al., 1991, Isolation of an additional member of the fibroblast growth factor receptor family, FGFR-3. *Proc. Natl. Acad. Sci. USA* 88:1095–1099), and FGFR4 (Partanen et al., 1991, FGFR-4, a novel acidic fibroblast growth factor receptor with a distinct expression pattern. *EMBO J.* 10:1347–1354) all contain three immunoglobulin (1 g)-like extracellular domains (Williams et al, 1988, The immunoglobulin superfamily-domains for cell surface recognition. *Ann. Rev. Immunol.* 6:381–405). The first Ig-like domain may or may not be present due to alternative splicing, resulting in either a two or three loop variant (Mansukhani et al., 1990, A murine fibroblast growth factor (FGF) receptor expressed in CHO cells is activated by basic FGF and Kaposi FGF. *Proc. Natl. Acad. Sci. USA* 87:4378–4382; Fujita et al., 1991, The expression of two isoforms of the human fibroblast growth factor receptor (fig) is directed by alternative splicing. *Biochem. Biophys. Res. Comm.* 174:946–951). This first loop has no effect on ligand binding and its function remains unknown (Johnson et al., 1990, supra; Mansukhani et al., 1990, supra). The genes of FGFR1 and FGFR2 contain three consecutive yet mutually exclusive exons that encode the 3' half of the last Ig-like domain (Champion-Arnaud et al., 1991, Multiple mRNAs code for proteins related to the BEK fibroblast growth factor receptor. *Oncogene* 6:979–987; Eisemann et al., 1991, Alternative splicing generates at least five different isoforms of the human basic-FGF receptor. *Oncogene* 6:1195–1202; Johnson et al., 1991, The human fibroblast growth factor receptor genes: A common structural arrangement underlies the mechanisms for generating receptor forms that differ in their third immunoglobulin domain. *Mol. Cell. biol.* 11:4627–4634; Yayon et al., 1992, A confined variable region confers ligand specificity on fibroblast growth factor receptors: Implications for the origin of the immunoglobulin fold. *EMBO J.* 11:1885–1890). Alternative splicing in this region generates secreted forms of these receptors and receptors with differences in their FGF binding specificities. Splicing of the first of the three exons (IIIa) into the mRNA results in a secreted form of the receptor containing no transmembrane or PTK domain (Johnson et al., supra., 1990, 1991). If the next exon (IIIb) is spliced into the mRNA, a membrane spanning PTK receptor with a high affinity for aFGF and KGF results. When considering FGFR2, this isoform is referred to as the KGF receptor (Miki et al., 1991, Expression cDNA cloning of the KGF receptor by creation of a transforming autocrine loop. *Science* 251:72–75; 1992, Determination of ligand-binding specificity by alternative splicing: Two distinct growth factor receptors encoded by a single gene. *Proc. Natl. Acad. Sc. USA* 89:246–250; Yayon et al., 1992, supra). Inclusion of the last of these three exons (IIIc) confers high affinity to aFGF, bFGF and FGF-4 (Dionne et al., 1990, supra; Mansukhani et al., 1992, Characterization of the murine BEK fibroblast growth factor (FGF) receptor: Activation by three members of the FGF family and requirement for heparin. *Proc. Natl. Acad. Sci. USA* 89:3305–3309) but not to KGF (Miki et al., 1992, supra). This FGFR2 isoform is referred to as a "bek-like" receptor.

Expression patterns of several FGF proteins during development are well documented (Whitman et al., 1989, Growth factors in early embryogenesis. *Annu. Rev. Cell Biol* 5:93–117; Hebert et al., 1990, Isolation of cDNAs encoding four mouse FGF family members and characterization of their expression patterns during embryogenesis. *Dev. Biol.* 138:454–463; Niswander et al., 1992, FGF-4 expression during gastrulation, myogenesis, limb and tooth development in the mouse. *Development* 114:755–768; Tannahill et al., 1992, Development expression of the Xenopus int-2 (FGF-3) gene: Activation by mesodermal and neural induction. *Development* 115:696–702). The FGFs have also been implicated in amphibian limb regeneration but their specific role in this developmental process remains obscure. When FGF is infused into the distal stump of denervated newt limbs, cell cycling is stimulated over the depressed level normally seen after denervation (Mescher et al, 1979, Mitogenic effect of a growth factor derived from myelin on denervated regenerates of newt forelimbs. *J. Exp. Zool.* 207:497–503; Gospodarowicz et al., 1980, Fibroblast growth factor and the control of vertebrate regeneration and repair. *Ann. N. Y. Acad. Sc.* 339:151–174). By binding assays and Western blotting analysis, (Boilly et al., 1991, Acidic fibroblast growth factor is present in regenerating limb blastemas of axolotls and binds specifically to blastema tissue. *Dev. Biol.* 145:302–310), showed that aFGF and its receptor(s) are present within the newt limb blastema; nevertheless, the cellular source of this growth factor was not determined. In the mouse limb bud, FGFR2 transcripts were detected in the surface ectoderm, whereas FGFR1 transcripts were distributed diffusely in the mesenchyme (Orr-Urtreger et al., 1991, Developmental expression of two murine fibroblast growth factor receptors, fig and bek. *Development* 113:1419–1434; Peters et al., 1992, Two FGF receptor genes are differentially expressed in epithelial and mesenchymal tissues during limb formation and organogenesis in the mouse. *Development* 114:233–243).

According to the present invention cDNAs of newt aFGF was isolated and characterized.

Accoding to the present invention, cDNAs of newt FGFR1 and FGFR2, FGFR3 and KGFR were cloned. Riboprobes made from these cDNAs were used to carry out in situ hybridization at various stages of newt limb regneration.

Further according to the present invention there is disclosed cells transfected with a DNA sequence encoding human acidic fibroblast growth factor and capable of expressing said factor.

An object of the present invention is to provide purified and synthetic forms of newt aFGF.

An additional object of the present invention is the determination of the amino acid sequence of such aFGF.

A further object of the present invention includes providing purified forms of newt aFGF and mammalian cell lines expressing FGF receptors which would be valuable to evalute angonist and antagonist proteins such as human FGF proteins.

DISCLOSURE OF INVENTION

The cDNA coding for the human full-length aFGF have been cloned (Bunnag et al., 1991, Transformed phenotype conferred to NIH/3T3 cells by ectopic expression of heparin-binding growth factor 1/acidic fibroblast growth factor. In *Vitro Cell. Dev. Biol.* 27A:89–96; Chiu et al., 1990, Alternative splicing generates two forms of mRNA coding for human heparin-binding growth factor 1. *Oncogene* 5:755–762). A number of others have also cloned and expressed human aFGF.

During the characterization of the cell lines expressing human full-length aFGF (Bunnag et al., 1991, supra) the inventors herein surprisingly found that two cell lines (Tr31-5-1 and Tr33-1-2), unlike their predecessor, do not respond to the mitogenic stimulation of full-length aFGF but still respond to truncated aFGF. According to the present invention cell lines are generated that will or will not respond to stimulation by aFGF. These cell lines are useful for the identification of agonists and antagonists of aFGF and other FGF proteins. Also, according to the present invention, FGF and FGF receptor (FGFR) cDNAs were isolated from species distant from human. An amphibian species commonly known as newt or salamander (*Notophthalamus viridescens*), known to regenerate their limbs after amputation, was chosen.

The present invention thus relates to novel newt aFGF cDNA and sequence, newt FGFR1 cDNA and sequence, newt FGFR2 cDNA and sequence, newt FGFR3 cDNA and sequence, newt KGFR cDNA and sequence, CHO-K cell lines (such as KPTr2-2) expressing newt KGFR, and mutant cell lines that become non-responsive to aFGF stimulation. These novel sequences and cell lines will substantially enhance the availability of acidic fibroblast growth factor.

The hatched box on the cDNA clones represents sequence that codes for the KGFR isoform (IIIb) whereas the cross-hatched box on clone 110 represents the bek-like (IIIc) isoform. The clones that are made contiguous with dashed lines represent cDNA's in which the first Ig-like domain is spliced out. Clone 301 represents the three loop form of newt FGFR2.

Figure 2B:
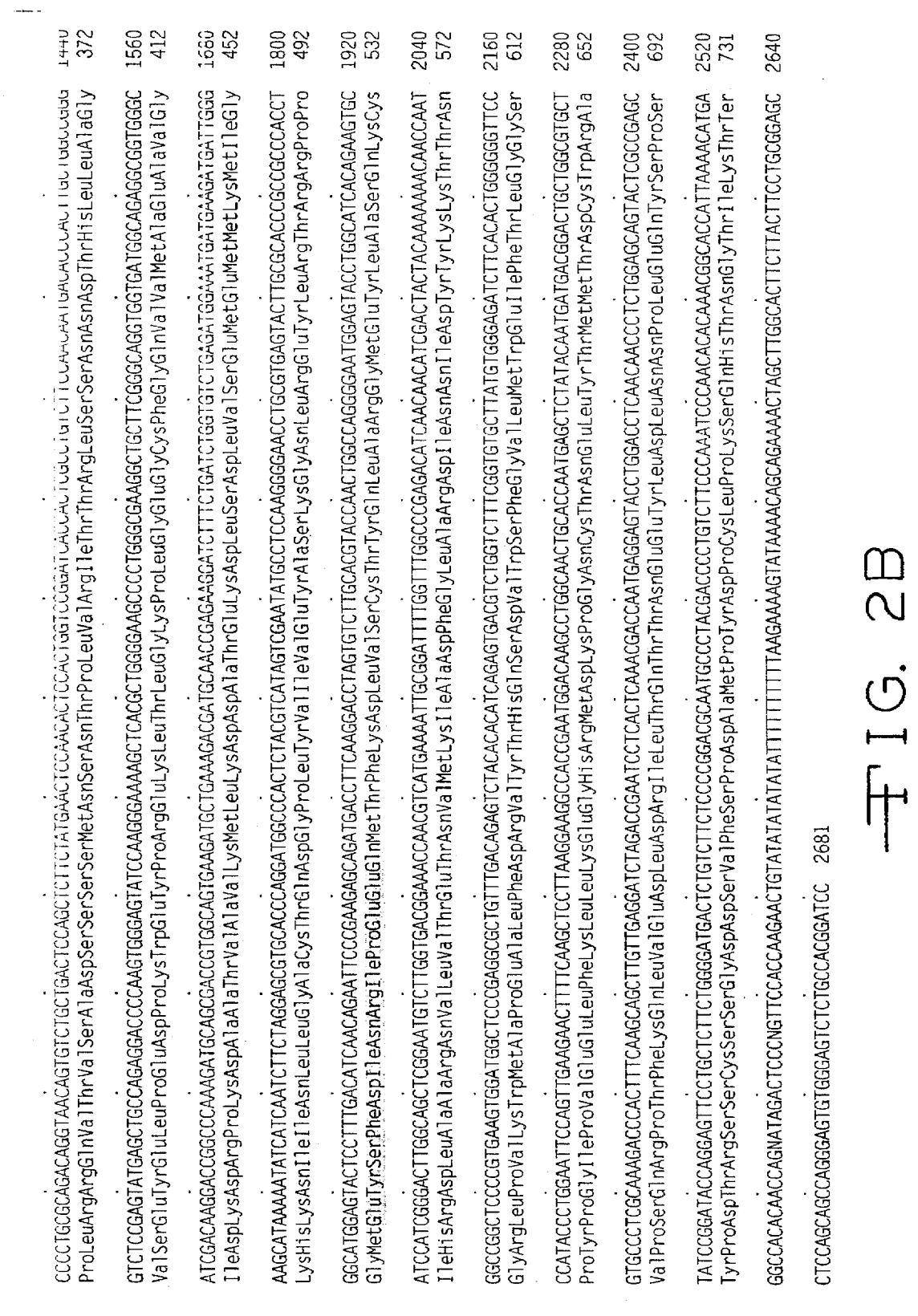

FIGS. 2A and 2B shows the nucleotide and predicted amino acid sequences of the newt FGFR2 cDNA (NvFGFR2). The hydrophobic signal sequence and transmembrane domain are double underlined. The single underline indicates potentially translated sequence. Bracketed amino acids indicate the immunoglobulin-like domain with the conserved cysteines indicated by asterisks. The alternatively spliced portion of the last Ig-like domain is indicated by a wavy underline. The amino acids of the protein tyrosine kinase domain are in parentheses and the kinase insert is highlighted. The sequence presented here is the KGFR variant of FGFR2.

FIGS. 3A, 3B and 3C show a comparison of the two amino acid sequences encoded by the second half of the last Ig-like domain. FIG. 3A shows alignment of the amino acid sequences encoded by the newt KGFR (clones 109, 301, 302, 310) and bek (clone 110) cDNA clones. FIG. 3B shows alignment of the amino acid sequences of newt and human KGFR. FIG. 3C shows alignment of the amino acid sequences of newt and human bek. The sequences were aligned using the DNASTAR Align program. The human sequences were obtained from Miki et al., 1991, supra and Dionne et al., 1990, supra.

Figure 4:
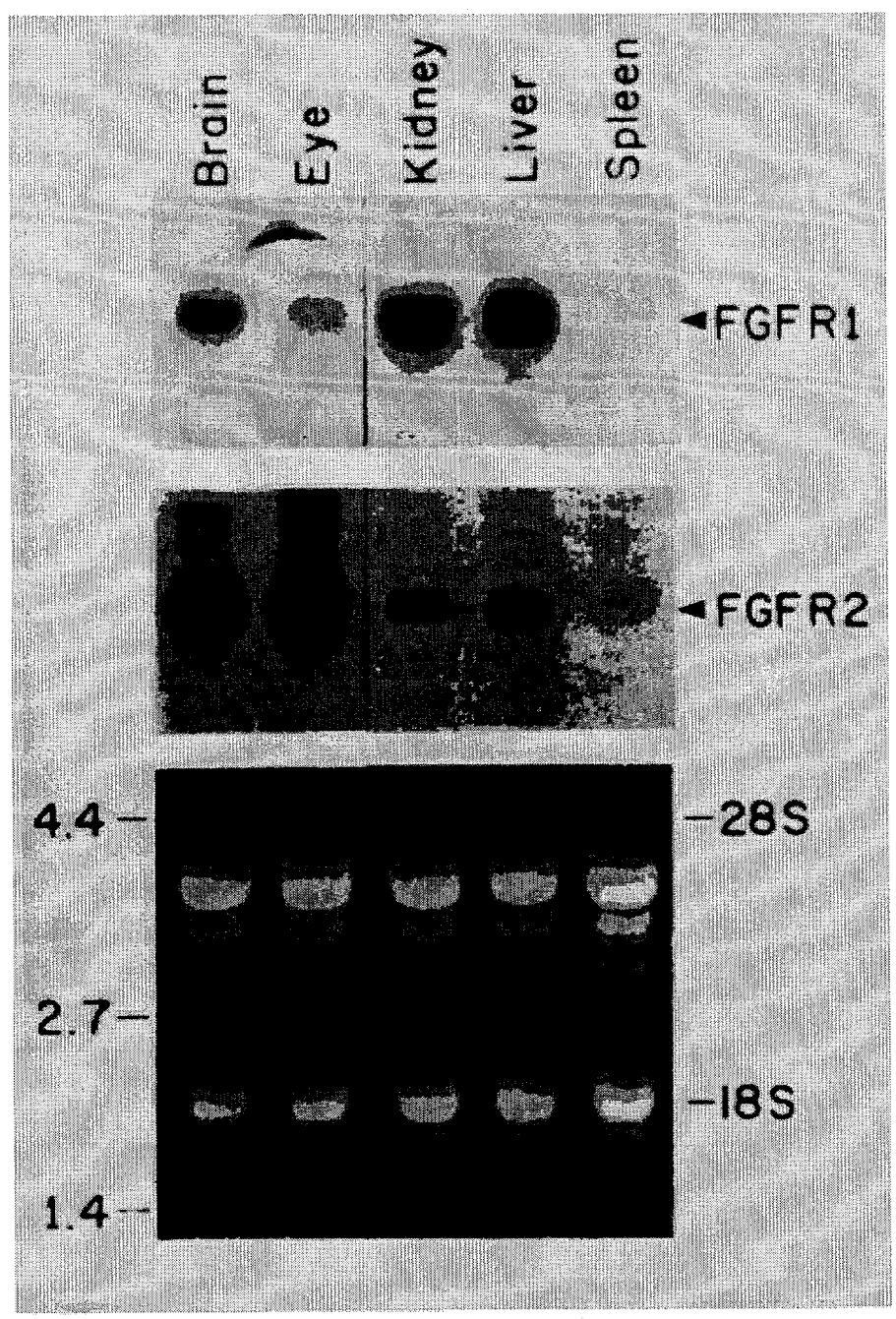

FIG. 4 shows a Northern blot analysis of newt tissues. Total RNA from newt brain, eye, kidney, liver, and spleen was hybridized to $^{32}$P-labled antisense riboprobes used in the in situ hybridizations. A single hybridizing band was observed using either the FGFR1 or FGFR2 riboprobes. The ethidium bromide stained agarose gel is shown to indicate loading the same amount of the RNA in each lane. The neural derived brain and eye express higher levels of the 6.5 kb FGFR2 mRNA while the mesodermally derived kidney and liver express higher levels of the 4.8 kb FGFR1 mRNA. The markers on the left are in kilobases (kb) and the 28S and 18S markers on the right are where the human large and small rRNA ran on the gel. Note that the newt large rRNA runs faster than the human 28S rRNA in the gel.

Figure 5A:
Figure 5B:

FIGS. 5A, 5B, 5C, 5D, 5E and 5F are micrographs illustrating the localization of FGFR2 mRNA in a pre-blastema regenerate. Anti-sense (A, C, and E) and sense (B, D, and F)$^{35}$S-labeled riboprobes were hybridized to cryosections of a day 10 pre-blastema stage regenerate and visualized by dark-field microscopy. FIGS. 5A and 5B show the hybridization of the anti-sense riboprobe to the basal layer of the wound epithelium (we), which is shown at higher magnification in FIG. 5C and FIG. 5D, and to the cells of the periosteum (black arrows) of the bisected bone (b), shown in FIGS. 5E and 5F under higher magnification. At this stage no signal is seen over the dedifferentiating mesenchyme cells. A, Bar=180 μm. C and E, Bar=70 μm.

Figure 6A:
Figure 6B:
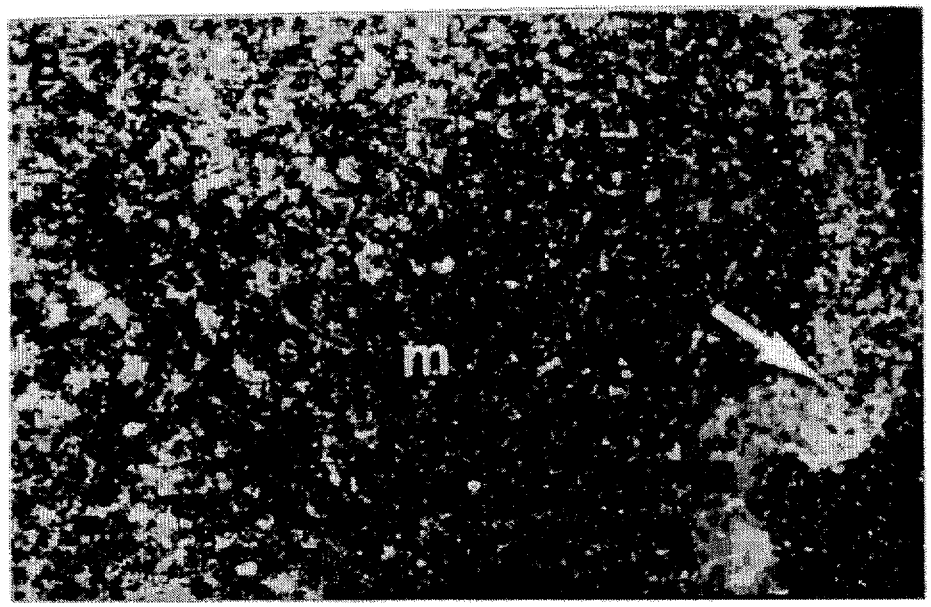

FIGS. 6A and 6B are dark-field micrographs showing the hybridization pattern of the anti-sense FGFR2 riboprobe to an early bud blastema at low (FIG. 6A) and high (FIG. 6B) magnification. The low-magnification in FIG. 6A shows FGFR2 transcripts in the cells of the basal layer of the wound epithelium (we) which decrease dramatically in the stump epidermis (white arrow marks border of wound epithelium and epidermis). FGFR2 mRNA is also seen in the mesenchymal cells (m) of the blastema closely associated with the bisected bones (b). The high-magnification of FIG. 6B shows that the FGFR2 mRNA is restricted to the wound epithelium and mesenchyme (m) and decreases abruptly at the amputation level (white arrow). Stump epidermis=e. A, Bar=180 μm; B, Bar=70 μm.

Figure 7:
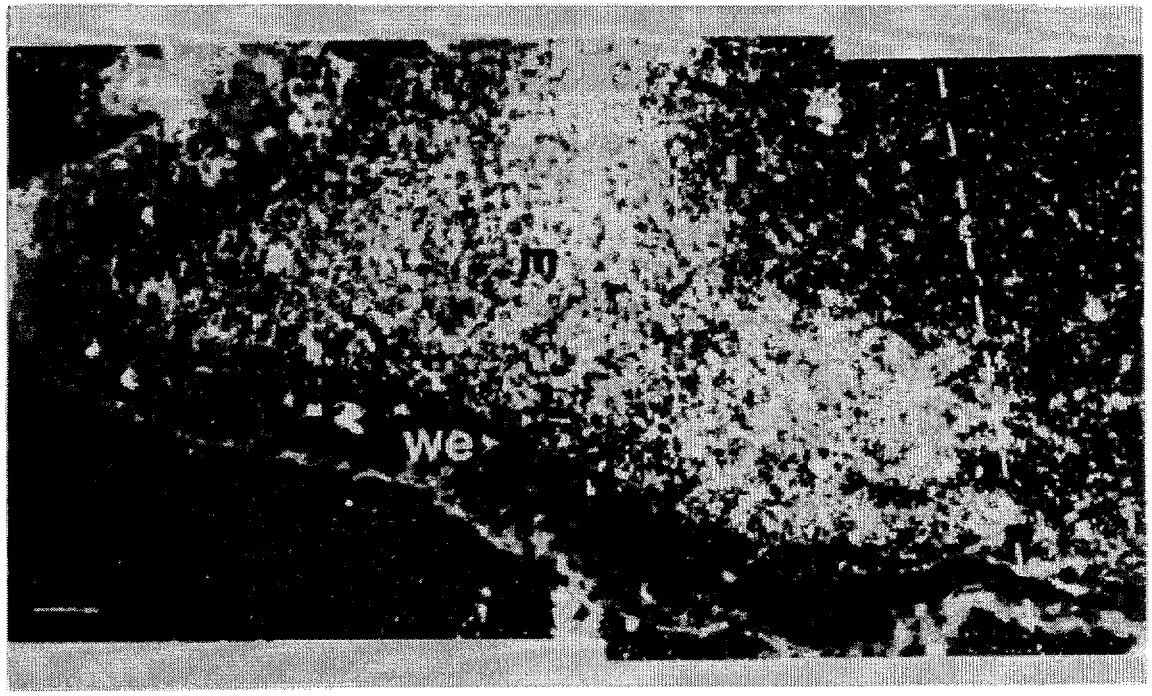

FIG. 7 is a micrograph illustrating hybridization of the FGFR1 anti-sense riboprobe in a mid bud blastema, visualized by dark-field microscopy. This micrograph shows the restricted localization of FGFR1 mRNA to the blastema mesenchyme (m) and its distinct absence from the wound epithelium (we) and stump tissue. The white dashed line indicates the level of amputation. Bar=70 μm.

Figure 8A:
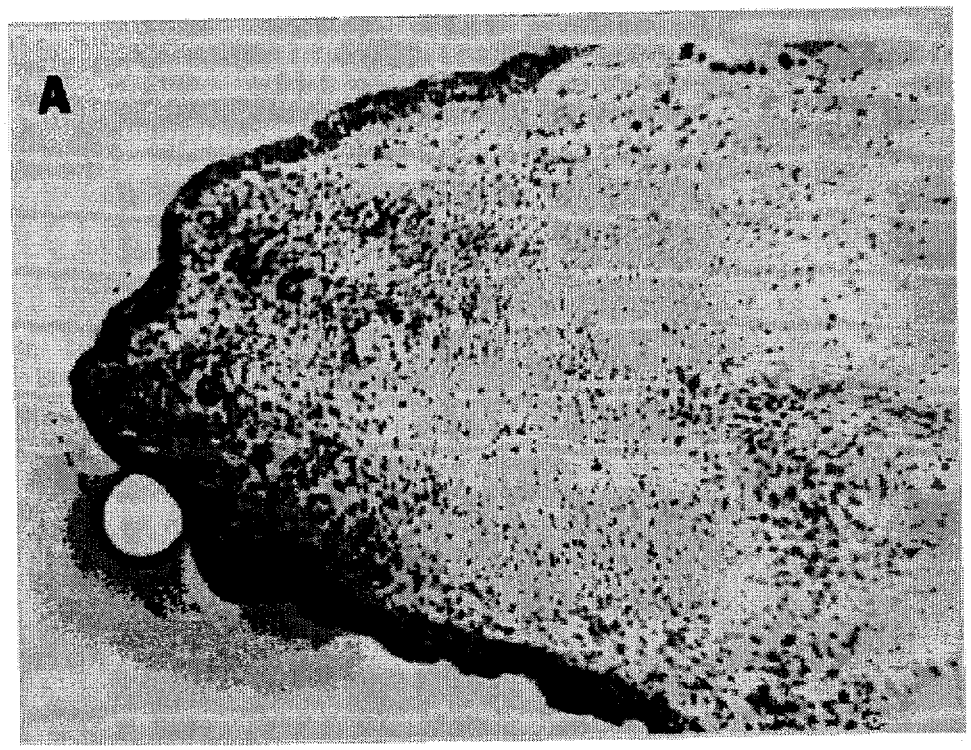
Figure 8B:

FIGS. 8A and 8B are light-field (FIG. 8A) and dark-field (FIG. 8B) micrographs of an early digit stage regenerate hybridized to the anti-sense FGFR2 riboprobe. The expression pattern is very specific to the cells of the condensing cartilage (c). Bar=175 μm.

Figure 9A:
Figure 9B:
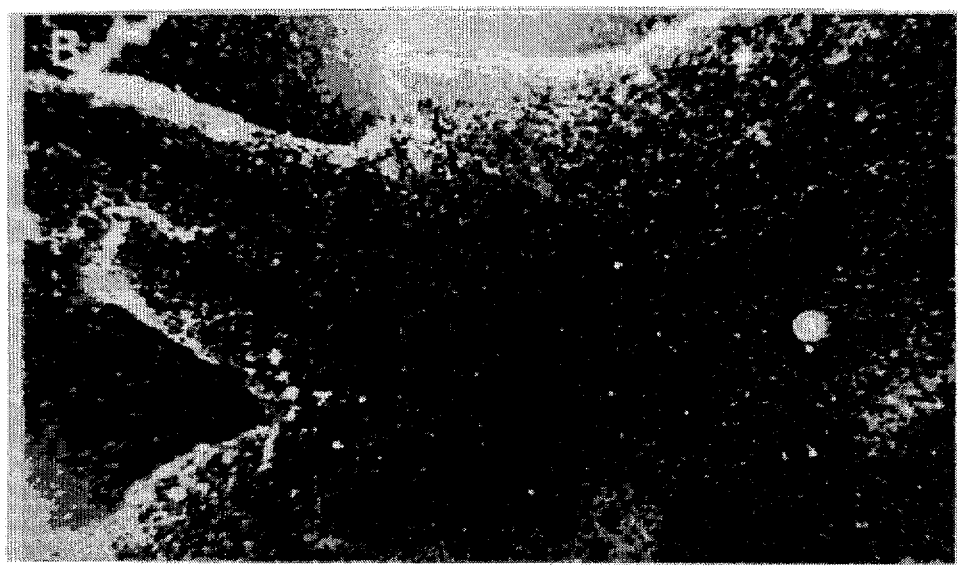

FIGS. 9A and 9B are dark-field micrographs showing the location of FGFR2 mRNA in a late digit regenerate, and the specificity of the FGFR2 riboprobe. The micrograph in FIG. 9A shows FGFR2 expression associated with the condensing cartilage (c) and the periosteum (white arrows). The micrograph in FIG. 9B is a section hybridized to the sense transcript. Bar =170 μm.

Figure 10:
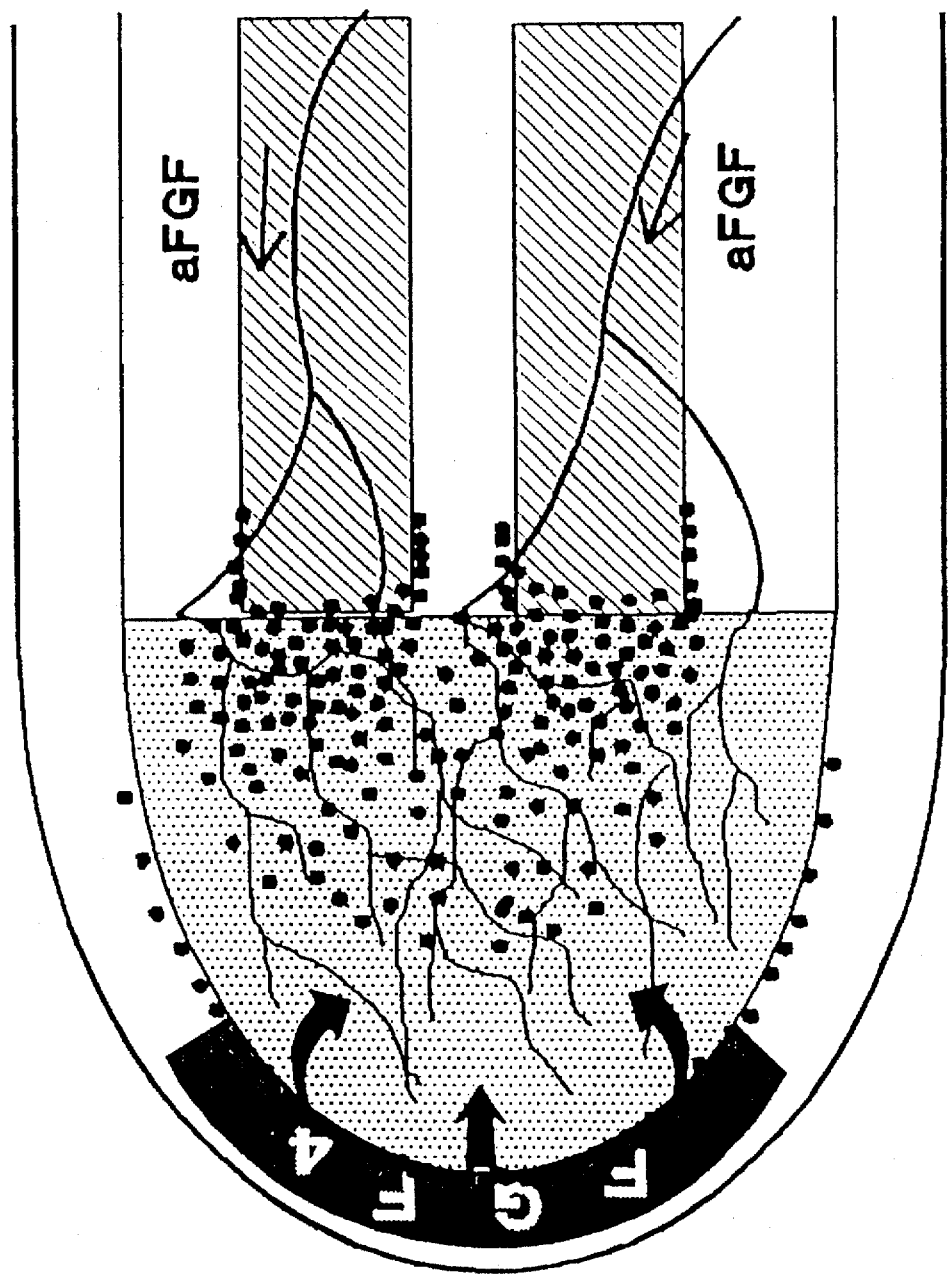

FIG. 10 is a diagram showing the interactions of FGFs and their receptors in regenerating limbs. FGFR1 is expressed by all blastema mesenchyme cells (light grey). FGFR2 is expressed by cells of the cartilage lineage and by basal cells of the wound epithelium (circles). Neurons synthesize aFGF which is transported by axons (thick lines) to blastema (as indicated by thin arrows) where it interacts with FGFR1 or FGFR2 on mesenchyme cells to stimulate their division. FGF-4 is produced by wound epithelium (dark grey) which also interacts with FGFR1 on mesenchyme cells (as indicated by thick arrows) to further stimulate cell division and/or to prevent differentiation. One of the FGFs interacts with FGFR2 to restrict cells to the cartilage lineage and/or to cause the FGFR2 expressing cells to form cartilage. FGFR2 expressed by the wound epithelium is involved in either FGF stimulation of wound epithelial cell cycling and/or in a specific function of the wound epithelium.

Figure 11:
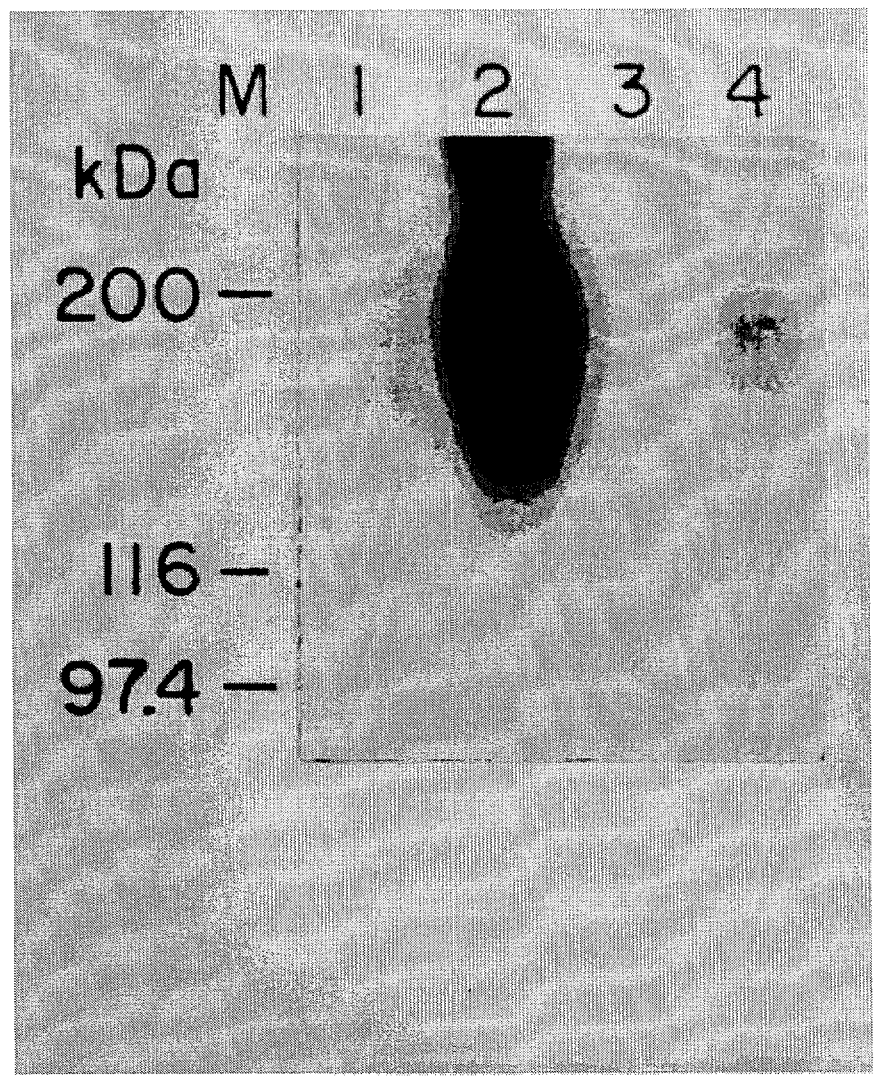

FIG. 11 shows crosslinking studies using CHO cells overexpressing newt KGFR cDNA. CHO cells transfected with pBJ5 vector (lane 1) or with newt KGFR expression vector (lanes 2–4) were crosslinked with $^{125}$I-aFGF using 0.3 mM disuccinimidyl suberate (DSS). Excess amounts (500-fold) of aFGF (lane 3) or KGF (lane 4) were used to compete with $^{125}$I-aFGF. Crosslinked products were analyzed on a 7.5% SDS-polyacrylamide gel.

Figure 12:
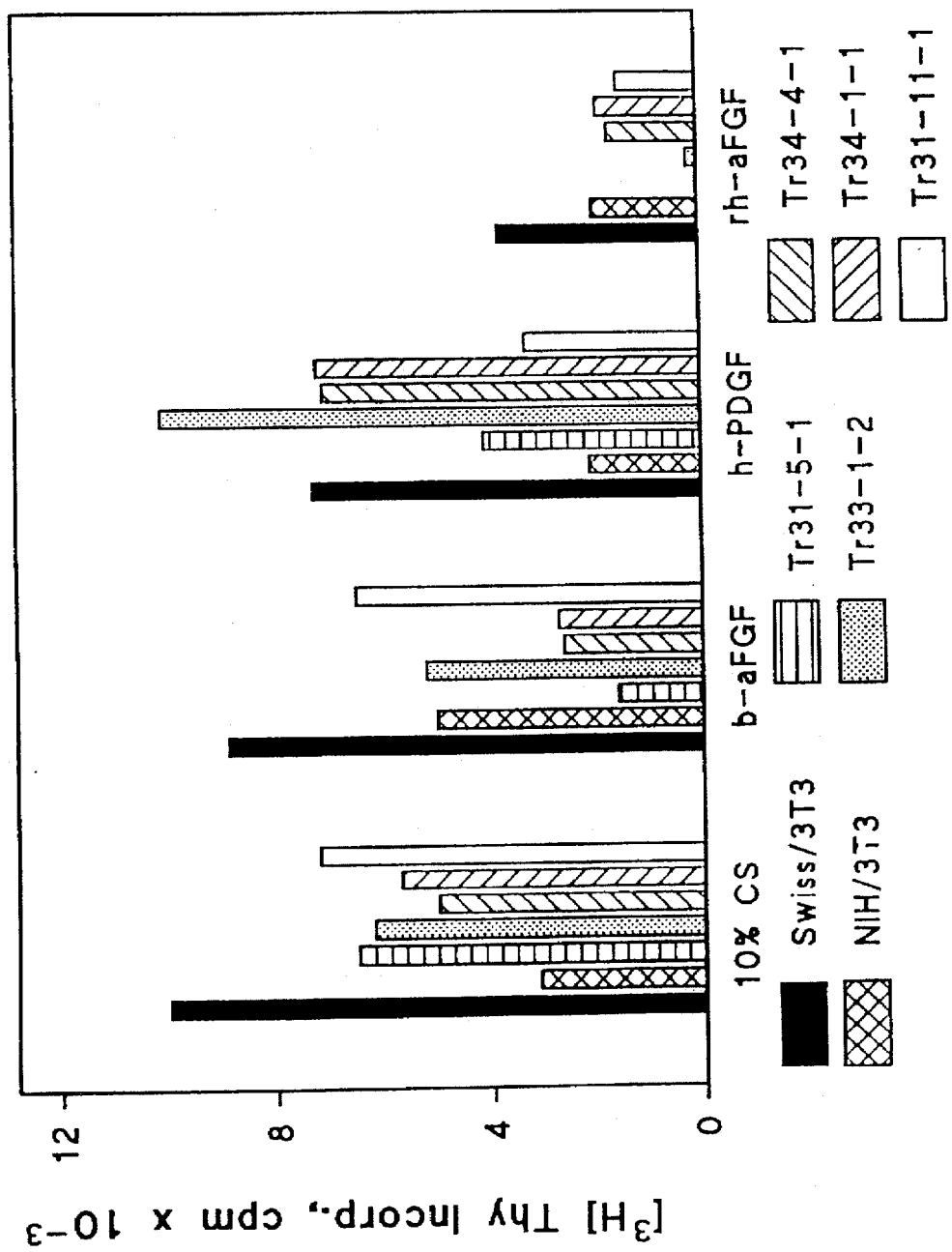

FIG. 12 is a graph showing the mitogenic effects of different growth factors to various transfected cell lines. Cells were grown to confluence, changed to Dulbecco's modified Eagle medium containing 0.5% calf serum and grown for two more days. Different growth factors or calf serum was then added to the medium to stimulate cells to grow. [$^3$H]thymidine was added 18 hours after addition of the mitogens and cells were incubated for another 6 hours. Bovine aFGF (b-aFGF) represents the truncated forms while human aFGF purified from Tr31-5-1 (rh-aFGF) represents the full-length protein. Cell lines, Tr31-5-1, 33-1-2, 34-1-1, and 34-4-1 are NIH/3T3 derivatives containing the aFGF cDNA construct in the positive orientation; whereas Tr31-11-1 contains aFGF cDNA in the anti-sense orientation.

DESCRIPTION OF INVENTION

The present invention has made it possible to provide readily available quantities of newt aFGF and newt FGFR fragments. As used herein FGF means fibroblast growth factor or its fragments produced by cell or cell-free culture systems. The FGF is in a bioactive form which means it has the capacity to influence cellular growth differentiation and survival as well as embryonic induction and angiogenesis.

Different alleles of FGF exist in nature. These variations are characterized by differences in nucleotide sequences of the structure gene coding for proteins of identical biological function. According to the present invention it is possible to produce analogs having single or multiple amino acid deletions, additions, substitutions or replacements. It is to be understood that all such allelic modifications, variations and analogs resulting in derivatives of FGF which retain the biologically active properties of newt FGF are included with the scope of this invention.

Further, according to the present invention expression vectors first two vectors which are capable of transcribing and translating DNA sequences contained within the vector where such sequences are linked to other regulatory sequences (such as promoters) capable of affecting the DNA sequence's expression. It is understood that these expression vectors are replicable in host organisms or systems as an integral part of the chromosomal DNA, as a bacteriophage or as an episome.

While the present invention discloses particular expression vectors which are particularly suitable for use in the invention, other expression vectors such as bacteriophages and viruses which normally inhabit and replicate in bacterial are useful. It is further understood that expression vectors such as plasmids or other forms of expression vectors which serve an equivalent function are suitable for use with the present invention.

The host cells useful with the present invention include various prokaryotic and eukaryotic organisms. Prokaryotic organisms such as E. coli are useful in the present invention. It is to be understood that other microbial strains which are compatible with the desired vectors can be utilized. It is to be understood that various control elements used for expression of foreign DNA sequences and combinations of these control elements can be used with the present invention.

Further host organisms include eukaryotic microbes such as yeast and cell lines derived from multi-cellular organisms. Various control elements useful in eukaryotic organisms and cell lines from multi-cellular organisms can be utilized with the present invention.

The principles for the present invention will be explained by this detailed description of the preferred embodiments together with the following examples.

A. Cloning of the Newt aFGF cDNA

The newt aFGF gene is too divergent from the human gene to be detected with heterologous probes in Southern hydridization. The newt aFGF cDNA was cloned by reverse transcription and polymerase chain reaction (RT-PCR). The degenerate synthetic oligonucleotides were designed from the most conservative region of aFGF among different species (upstream primer 306, 5'-TTY ACA GCN CTG ACN GAR AAR TTY AA-3'(SEQ ID NO. 11); downstream primer 603, 5'-TAG GTR TTR TAR TGR TTY TCY TC-3' (SEQ ID NO. 12); R=purine, Y=pyrimidine, N=any base) and carried out RT-PCR to isolate the aFGF cDNA from newt brain RNA. Newt brain total RNA (0.5 µg) was combined with 1.5 pM of the downstream primer and *Thermus thermophilus* (Tth) polymerase in the presence of 1 mM $MnCl_2$ and 200 µM dNTP. This was incubated for 15 min at 60° C. to allow the reverse transcription to take place. The upstream primer was then added at a concentration of 0.3 µM along with a Mn++chelator and $MgCl_2$ at a concentration of 2 mM to allow DNA polymerization to take place. The mixture was then cycled between 1 min at 94° C. and 1 min at 50° C. for 30 cycles. One fifth of the reaction mix was analyzed by electrophoresis on a 3% agarose gel followed by Southern analysis. The filter was hybridized with the human aFGF cDNA and a band of 300 bp was observed on the X-ray film but could not be visualized on the ethidium bromide stained gel. A second fifth was electrophoresed on a 3% agarose gel and the region between 280 and 340 bp was isolated and purified with Geneclean. A PCR reaction was then performed using 0.3 µM of both primers under the same cycling conditions above. One fifth was analyzed on a 3% agarose gel and a band of 310 bp was observed, isolated and subcloned into the SmaI site of pBluescript SK(+). Three subclones were completely sequenced and the results indicate that a 311 bp cDNA fragment representing the newt aFGF cDNA was isolated and characterized, as shown in Sequence ID No. 1 and 2.

B. Cloning of the Newt FGFR1 cDNA, FGFR2 cDNA, FGFR3 cDNA and KGFR cDNA.

According to the present invention, DNA sequences encoding all or part of the polypeptide sequence of newt fibroblast growth factor (NvFGFR1 and NvFGFR2) have been isolated and characterized as follows.

Figure 1:
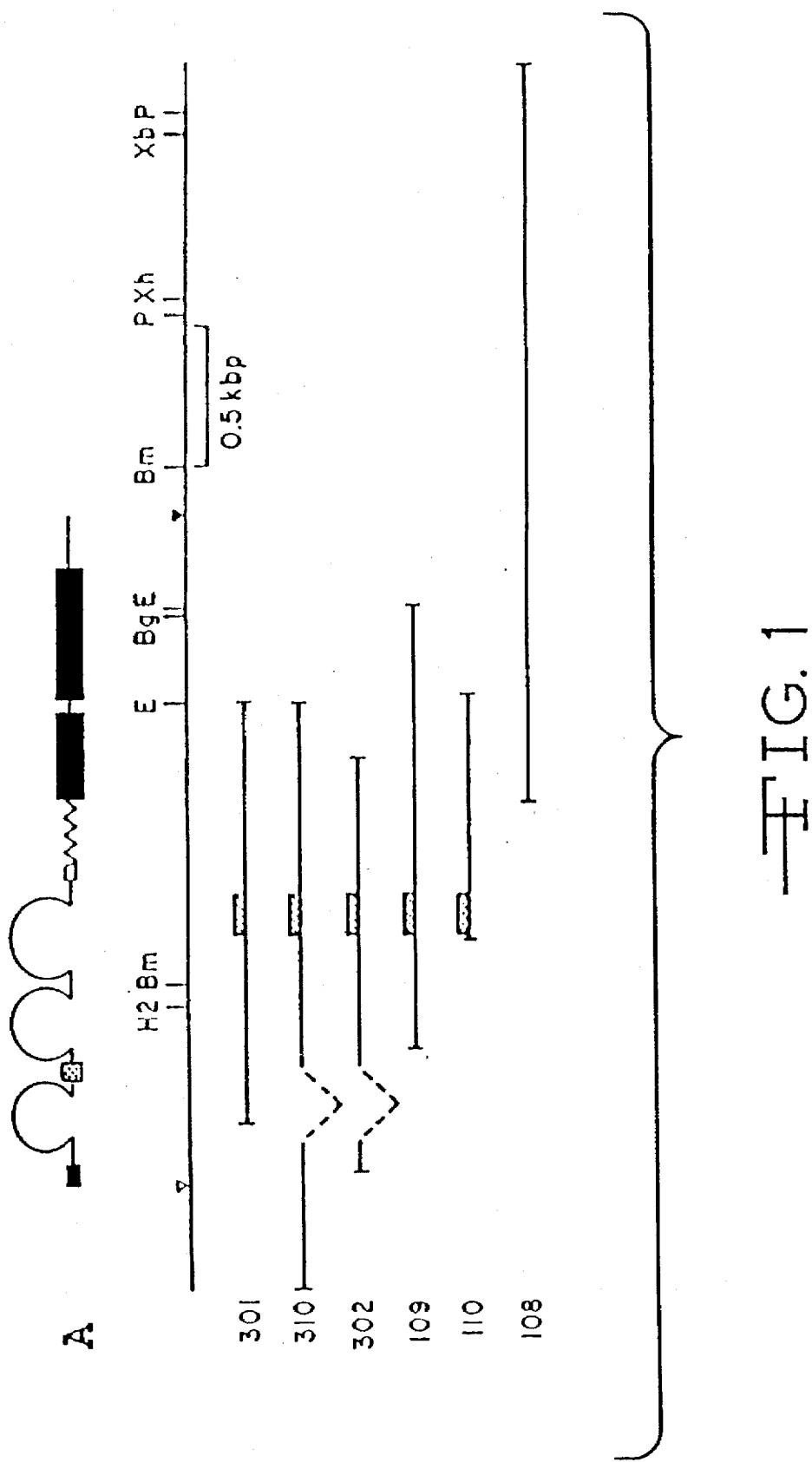
FIG. 1 is a representation of NvFGFR2 cDNA clones. The receptor molecule is graphically represented above the cDNA clones. The major restriction sites are shown between the graphic model and the cDNA clones (Bm=BamHI; Bg-=BgIII; E=EcoRI; H2=HindII; P=PstI; Xb=XbaI; Xh=XhoI). The model is drawn to linear scale in relation to the cDNA sequence. The open and closed triangles represent the initiation and termination codons, respectively. The three loop structures represent the immunoglobulin (Ig)-like extracellular domains and the verticle line bisecting the molecule between the first and second Ig-like domains represents the acidic domain. The open box followed by the wavy line represents the transmembrane and juxtamembrane domains and the closed box represents the tyrosine kinase domain bisected by the kinase insert.

A newt forelimb blastema cDNA library was screened under reduced stringency with a partial human cDNA fragment of the FGFR1 gene. Four lambda clones, 102, 108, 109 and 110, were purified and sequenced. The sequences show that three clones, 108, 109 and 110 overlap each other and are most homologous to the FGFR2 cDNAs of different species, as shown in FIG. 1 and in Table 1 below. The sequence of clone 102 indicates that this cDNA is most homologous to FGFR1 cDNAs of different species as seen in Table 1.

TABLE 1

| | Nucleotide sequence similarities between different members of the FGF receptor family | | | | | | |
|---|---|---|---|---|---|---|---|
| | (445-2556)[1] HUM FGFR1 | (794-2887)[2] HUM FGFR2 | (418-2460)[3] HUM FGFR3 | (410-2464)[4] HUM FGFR4 | (410-2515)[5] Ch FGFR1 | (485-2575)[6] Ch FGFR2 | (523-2571)[7] Ch FGFR3 |
| Newt FGFR1 (1-1176) | 77 | 72 | 69 | 61 | 76 | 71 | 69 |
| Newt FGFR2 (433-2517) | 69 | 78 | 68 | 62 | 69 | 78 | 68 |

The nucleotides used in the comparison are shown in parentheses and are taken from the following references: Dionne et al., 1990, Cloning and expression of two distinct high-affinity receptors cross-reacting with acidic and basic fibroblast growth factor. EMBO J. 9:2685–2692[1]; Miki et al., 1992[2], Determination of ligand-binding specificity by alternative splicing: Two distinct growth factor receptors encoded by a single gene. Proc. Natl. Acad. Sci. USA 89:246–250; Keegan et al., 1991[3], Isolation of an additional member of the fibroblast growth factor receptor family, FGFR-3. Proc. Natl. Acad. Sci. USA 88:1095–1099; Partanen et al., 1991[4], FGFR-4, a novel acidic fibroblast growth factor receptor with a distinct expression pattern. EMBO J. 10:1347–1354; Pasqua-e et al., 1989[5], Identification of a developmentally regulated protein-tyrosine kinase by using antiphosphotyrosine antibodies to screen a cDNA expression library. Proc. Natl. Acad. Sci. USA 86:5449–5452; Sato et al., 1991[6], Isolation of chicken-bek and a related gene; identification of structural variation in the ligand-binding domains of the FGF-receptor family. Oncogene 6:1279–1283; Pasquale, 1990[7], A distinctive family of embryonic protein-tyrosine kinase receptors. Proc. Natl. Acad. Sci. USA 87:5812–5816. The alignments and percent similarity were determined using DNASTAR's ALIGN program.

These clones all contain the cytoplasmic tyrosine kinase domain but are truncated in the extracellular ligand binding domain. Two of the newt FGFR2 clones, 109 and 110, also contain a region in the 3' half of the distal Ig-like domain that vary between them. These variants represent the newt cognates of two different isoforms of FGFR2, one homologous to bek the other to the KGFR. To obtain full-length FGFR2 cDNA clones, the 5' portion of clone 109 (240 bp EcoRI-BamHI) was used to rescreen the blastema cDNA library and three more cDNA clones were isolated, purified and sequenced. Clones 302 and 310 represent the two Ig-like loop variant of FGFR2 while Clone 301 represents a truncated form of the three loop form of FGFR2. All three 300 series cDNA clones are of the KGFR isoform.

The predicted amino acid sequence for the newt two Ig-like loop variant of KGFR is shown in FIGS. 2A and 2B (Sequence ID No: 9 and 10). The sequence in the 3'-half of the last Ig-like domain represents that of the KGFR isoform, as shown in FIGS. 2A and 2B and 3. FIG. 3A shows the difference between the newt KGFR-like and bek-like forms of FGFR2.

The amino acid alignment, as well as the nucleotide sequence comparisons, show that the flanking regions of these cDNAs are identical whereas the region in between shares 58% amino acid similarity. It is noted that the sequence similarity is greater, 73% and 78%, respectively, as shown in FIGS. 3B and 3C, between the same isoforms of different species (newt KGFR vs. human KGFR and newt bek vs. human bek) than between the different isoforms of the same species (FIG. 3A). Sequence ID numbers for the DNA and predicted amino acid sequence of the bek-like newt FGFR2 are 5 and 6, respectively.

The overall sequence similarity of the newt KGFR and the truncated newt FGFR1 (Sequence ID No: 3 and 4) cDNA with other human and chicken FGFR cDNAs is shown in Table 1. When the newt FGFR1 is compared with other FGF receptors, the closest similarity is with FGFR1 from other species, 77% with human and 76% with chicken FGFR1. Likewise, the newt KGFR form of FGFR2 is closest to other FGFR2 cDNA's, 78% to both human and chicken FGFR2.

In another library screening, clone 103 (a.k.a. MJ3-1) was isolated. Sequencing analysis of MJ3-1 showed that it is most homologous to FGFR3 cDNAs of human and mouse, and therefore designated NvFGFR3 (Sequence ID Nos. 7 and 8).

Northern Hybridization—As a first step toward determining the FGFR expression pattern and specificity of the riboprobes, Northern analysis on various newt tissues was carried out. The FGFR1 and FGFR2 antisense riboprobes used for the in situ were hybridized to newt brain, eye, kidney, liver, and spleen total RNA. A single band of 4.8 kb was observed in these tissues with the FGFR1 riboprobe with the kidney and liver showing the highest intensity of signal. When the same filter was stripped and hybridized to an FGFR2 riboprobe, a single band of 6.5 kb was observed with the brain and eye showing the highest level of hybridization, as shown in FIG. 4.

In Situ Hybridization—Cryosections of regenerating newt limbs of different stages staged according to (Iten et al., 1973, Forelimb regeneration from different levels of amputation in the newt, N. viridescen: Length, rate, and stages. Wilhelm Roux Arch. 173:263–282), were hybridized to both sense and antisense $^{35}$S-labeled riboprobes, washed and exposed to photographic emulsion. The slides were developed, stained with hematoxylin and counterstained with eosin, and examined under both light- and dark- field microscopy. The fragment used to generate the FGFR2 riboprobes was a 306 bp BbsI-BamHI fragment containing the second Ig-like extracellular domains (nt. 465–770 in FIG. 2A and 2B). This antisense riboprobe recognizes all known isoforms, generated by alternative splicing, of newt FGFR2. The newt FGFR1 specific riboprobe represents the last 73 amino acids of the carboxyl terminus and 80 nucleotides of 3'-untranslated sequence.

Figure 5C:
Figure 5D:
Figure 5E:
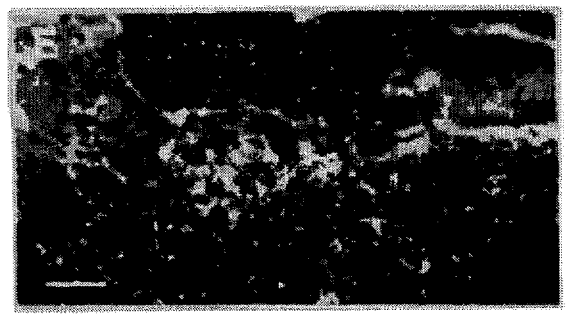
Figure 5F:

At the pre-blastema stage of regeneration there were two FGFR2-hybridizing regions observed in the regenerate, as shown in FIG. 5A. The first region was in the wound epithelium. At this stage, the wound epithelium was 5–10 cell layers thick and the hybridization was seen in the basal cells adjacent the underlying mesenchyme but not in the outer layers, as shown in FIG. 5C. This hybridization did not extend into the limb epidermis and thus was specific for the wound epithelium. Additional hybridization was also observed in the cells of the periosteum, as shown in FIG. 5E. At this stage no signal is detected over the dedifferentiating mesenchyme cells, as shown in FIG. 5A. The hybridization signals are specific to the FGFR2, since the sense probe revealed negligible signals in the wound epithelium and periosteum, as shown in FIGS. 5B, 5D and 5F.

The early bud blastema showed three distinct hybridization areas. The first was the basal layer of the wound epithelium, shown in FIG. 6A, as seen in the pre-blastema stage shown in FIG. 5. At a higher magnification, it was apparent that the hybridization signal decreases abruptly at the amputation boundary, as shown in FIG. 6B.

The second was in the blastema mesenchyme but was largely restricted to cells in the core of the blastema adjacent the ends of the bisected bones as shown in FIG. 6A. In contrast, little hybridization was seen in the more distal mesenchymal cells adjacent the wound epithelium. The third area of hybridization was in the periosteum, observed in the stump (FIG. 6A) as in the pre-blastema stage regenerate.

The mid bud blastema showed the same pattern of hybridization to FGFR2 as the early bud blastema but a greater intensity of signal was seen in the blastema mesenchyme, probably due in part to the increased cell number at this stage of regeneration. The hybridization signal seen in the basal cell layer of the wound epithelium remained unchanged. At this same stage, the FGFR1 hybridization pattern was restricted to the blastema mesenchyme and appeared to be homogeneously distributed throughout the blastema, as shown in FIG. 7. In contrast to the FGFR2-hybridizing pattern, there was no apparent FGFR1 hybridization in the wound epithelium as shown in FIG. 7.

As growth slowed and differentiation began, a different pattern of hybridization to FGFR2 emerged. Hybridization was now concentrated in the condensing cartilage and followed the pattern of the forming digits. The wound epithelial expression of FGFR2 detected early in the pre-blastema stage, which lasted till the mid-bud stage, was no longer observed, as shown in FIG. 8. As differentiation continued into the digit stages of regeneration, the pattern of hybridization to FGFR2 became more restricted to the perichondrial regions of the forming digits and metacarpals, with less intense hybridization remaining in the pre-ossified cartilage of the regenerate, as shown in FIG. 9.

The newt FGF receptors 1 and 2 (NvFGFR1 and NvFGFR2) are both expressed in the blastema during forelimb regeneration. However, the temporal and spatial expression patterns of these receptors are different, indicating that the two receptors may have different roles. FGFR1 expression is restricted to the blastema mesenchyme and appears to be homogeneously distributed throughout the blastema. FGFR2 is expressed in the core of the blastema adjacent and surrounding the bisected bone, as well as in the basal layer of cells in the wound epithelium during the stages of regeneration associated with growth and blastema cell proliferation.

During differentiation stages, FGFR2 expression is predominantly seen in the condensing cartilage of the early digit stage and in the perichondrium of the late digit stage. FGFR1 is a receptor for aFGF, bFGF and FGF-4; FGFR2 is a receptor for aFGF and either bFGF or KGF, depending on the isoform. Thus, it is now believed that blastema cells respond to different FGF ligands. The cellular source of various members of the FGF growth factor family is shown in FIG. which describes a testable model to account for a multiplicity of FGF's and FGFR's in regenerating limbs. This model is established based on the in situ hybridization results disclosed herein for the FGFRs shown here and on other results for the FGFs.

The relative levels of receptor mRNAs in the different newt tissues are also different as shown by Northern analyses. FGFR1 is expressed at higher levels in the mesodermally derived kidney and liver than in the neurally derived brain and eye. There is no expression of this receptor in the spleen. FGFR2, on the other hand, is expressed at higher levels in the brain and eye than in the kidney and liver and expression is detectable in the spleen. FGFR1 expression seems to correlate strongly with mesodermal tissues as seen in the kidney and liver by Northern hybridization, as shown in FIG. 4, and in the blastema mesenchyme observed by in situ hybridization, as shown in FIG. 7. FGFR2, on the other had, is shown to be expressed at high levels in nervous tissue by Northern hybridization. It is now believed that the expression of FGFR2 in the blastema, as seen by in situ hybridization, is in response to the neurotrophic factor(s) released into the blastema by nerves.

In developing mouse limbs, FGF-4 is expressed in the apical ectodermal ridge (AER) and, since FGF-4 has a signal peptide and can therefore be secreted, it was suggested that the target of FGF-4 is the limb mesenchyme (Niswander et al, 1992, supra). It is likely that the AER and the wound epithelium carry out similar functions, i.e., epithelial/mesenchymal interactions, essential for limb bud development and blastema outgrowth, respectively (Muneoka et al., 1992, Molecular aspects of regeneration in developing vertebrate limbs, *Dev. Bio.* 152:37–49). Thus, the wound epithelium may also release FGF-4 into the mesenchyme where it interacts with FGFR1 and stimulates mesenchyme growth, as shown in FIG. 10. Another possible source of one or more FGFs is the nerve. Nerves are essential for limb regeneration (Singer, 1952, The influence of the nerve in regeneration of the amphibian extremity. *Q. Rev. Biol.* 27:169–200) but the identity of the putative neurotrophic factor(s) is not yet known (Carlone et al., 1985, Trophic factors from nerves. *Regulation of Vertebrate Limb Regeneration*, (ed. R. E. Sicard), pp. 93–105. Oxford University Press, New York). It has been shown that a crude FGF preparation exhibited some mitogenicity when infused into denervated newt limb stumps (Mescher et al, 1979, supra;

Gospodarowicz et al., 1980, supra). In mice, it was shown that aFGF mRNA is present in ganglia by in situ hybridization and that aFGF is present within peripheral nerves closely associated with the cytoplasmic side of the axonal membranes by immunohistochemical studies (Elde et al., 1991, Prominent expression of acidic fibroblast growth factor in motor and sensory neurons. *Neuron* 7:349–364). Moreover, aFGF is present in the blastema during limb regeneration in axolotis (Boilly et al., 1991, supra). Thus, it is possible that during blastema development aFGF is released from nerves into the blastema where it can react with mesenchymal cells expressing FGFR1, and with the cells that are expressing FGFR2 in the core of the blastema adjacent the bisected bone. It may also interact with the cells within the wound epithelium that are expressing FGFR2 (FIG. 10). A recent demonstration of multiple tissue-specific promoters in the aFGF gene (Myers et al, 1993, Gene structure and differential expression of acidic fibroblast growth factor mRNA: identification and distribution of four different transcripts. *Oncogene* 8:341–349) lends credence to the theory that the aFGF gene may be equipped with the flexibility to respond to various developmental or traumatic situations.

The expression pattern of FGFR2 raises the possibility that this receptor is restricted to the cartilage lineage. The expression of FGFR2 in the blastema is seen initially in those cells closely associated with the bisected ends of the radius and ulna. Subsequently, FGFR2 expression is associated with mesenchymal cells condensing to form the skeletal promordia. Utilizing triploidy and thymidine-labeled grafts of either cartilage or muscle, Steen, 1968, Stability of chondrocyte differentiation and contribution of muscle to cartilage during limb regeneration in the axolotl (*Siredon mexicanum*). *J. Exp. Zool.* 167:49–78), showed that in axolotls, the cartilage lineage is very stable; most cartilage cells give rise to blastema cells that then redifferentiate back into cartilage. It has also been shown that connective tissue cells can give rise to cartilage (reviewed in Bryant et al., 1992, Retinoic acid, local cell-cell interactions and pattern formation in vertebrate limbs. *Dev. Biol.* 152:1–25). While lineage studies have not been done in newts, the inventors believe that periosteal cells contribute to the blastema cartilage lineage. This view is supported by the inventors' observation in unamputated limbs (data not shown) and in the limb stump (FIG. 5E) that FGFR2 is expressed in periosteal cells and in cartilage of the epiphyses of the radius and ulna and in the autopodium. Thus, chondrocytes and periosteal cells already expressing FGFR2 may be recruited into the blastema early in regeneration and then largely maintained in the cartilage lineage. In this regard, Gospodarowitz et al., 1980, supra, showed that FGF preparations can stimulate chondroblast proliferation. Also, aFGF has been isolated from bovine scapular cartilage (Sullivan et al., 1985, Purification of cartilage-derviced growth factor by heparin affinity chromatography. *J. BioL Chem.* 260:2399–2403) and bone (Hauschka et al., 1986, Growth factors in bone matrix. Isolation of multiple types by affinity chromatography on heparin sepharose. *J. Biol. Chem.* 261:12665–12674). Perhaps in regeneration, aFGF interacts with FGFR2 to stimulate chondroblast proliferation and/or to maintain the cartilage lineage.

The results shown herein suggest that FGFR2 also play a role in specific functions of the wound epithelium and/or in wound epithelial development into skin. It is shown herein that FGFR2 expression is observed in the basal layer of the wound epithelium during pre-blastema stages and this expression persists until differentiation stages. In the developing mouse, the entire body ectoderm, including the limb bud ectoderm, expresses FGFR2 (Orr-Urtreger et al., 1991, supra; Peters et al., 1992, supra) suggesting that FGFR2 is important for normal development of skin. In a wound healing study, KGF was shown to be induced 160 fold one day after skin injury (Werner et al., 1992, supra). This large induction was unique within the FGF family, since mRNA levels of aFGF, bFGF and FGF-5 were induced only 2- to 10-fold during wound healing, and there was no expression of FGF-3, FGF-4 and FGF-6 detected in normal and wounded skin. In situ hybridization showed expression of KGF in the dermis while FGFR2 was predominatly expressed in the epidermis (Werner et al., 1992, supra). The spatial and temporal patterns of expression of FGFR1 and FGFR2 (FIGS. 5–9) during limb regeneration are reminiscent of those seen in embryonic limb development (Orr-Urtreger et al., 1991, supra; Peters et al., 1992, supra). Furthermore, at the initial stage of blastema formation, the distribution of the FGF receptors in the wound epithelium duplicate those seen in the back skin wounding model (Werner et al., 1992, supra).

The wound epithelium is a necessary component of the regenerate (Singer et al, 1961, supra) and has been shown to express a number of molecules not expressed by skin epidermis, including the antigens designated WE3 (Tassava et al., 1986, Regenerate epithelium and skin glands of the adult newt react to the same monoclonal antibody. *J. Exp. Zool.* 239:229–240), WE4 (Castilla et al., 1992, Extraction of the WE3 antigen and comparison of reactivities of mAbs WE3 and WE4 in adult newt regeneration epithelium and body tissues. In *Keys for Regeneration*, (ed. C. H. Taban and B. Boilly), vol. 23, pp. 116–130. Karger, Basel.), MT1/tenascin (Onda et al., 1991, Characterization of a newt tenasin cDNA and localization of the tenascin mRNA during newt limb regeneration by in situ hybridization. *Dev. Biol* 148:219–232), and MT2 (Klatt et al., 1992, Monoclonal antibody MT2 identifies an extracellular matrix glycoprotein that is co-localized with tenascin during adult newt limb regeneration. *Differentiation* 50:133–140). The interaction of FGFR2 with its ligand is involved with the synthesis and/or function of these wound epithelial antigens. Finally, while innervation of the wound epithelium is not essential for regeneration (Sidman et al., 1960, Limb regeneration without innervation of the apical epidermis in the adult newt, Triturus. *J. Exp. Zool.* 144:105–110, an FGF-like neurotrophic factor released from nerves may nevertheless interact with FGFR2 in the wound epithelium, either in stimulating proliferation or in establishing a functional wound epithelium. Thus, the results herein show that heterogeneity exists in the expression patterns of FGFR1 and FGFR2 during limb regeneration in newts.

This invention will now be illustrated by the following examples. Adult newts, *Notophthalmus viridescens*, were collected in southern Ohio, maintained in aged tap water at room temperature, and fed raw beef liver four times a week. Limbs were amputated through the midradius/ulna and protruding bones were trimmed to the level of soft tissues. Newts were then returned to water and allowed to regenerate to the desired stage. Regenerates were collected at 5 and 10 days after amputation (preblastema stages), and at early-bud, mid-bud, late-bud, palette and digit stages (staged according to Iten et al., 1973, supra). From two to six limbs/regenerates were sampled at each stage. Operations were performed while animals were anesthetized with MS-222 (ethylm-aminobenzoate methanesulfonate; Sigma, St. Louis, Mo.).

Cloning and Sequencing of Newt FGFR1 and FGFR2

A 2.0 kbp EcoRI fragment from a human FGFR1/fIg cDNA clone (Ruta et al., 1988, A novel protein tyrosine kinase gene whose expression is modulated during endothelial cell differentiation. *Oncogene* 3:9–16), was used to screen a newt mid-bud blastema cDNA library constructed in λgt 11 (Ragsdale et al., 1989, Identification of a novel retinoic acid receptor in regenerative tissues of the newt. *Nature* 341:654–657). A total of $5 \times 10^5$ plaques ($5 \times 10^4$ plaques/150 mm plate) were transferred to duplicate nitrocellulose filters (Schleicher & Schuell) and hybridized to a random primed human FGFR1 cDNA probe under low stringency (43% formamide, 5×SSC, 5×Denhardt's solution, 1% SDS, 200 µg/ml salmon sperm DNA in 50 mM phosphate buffer, pH 6.5 at 37° C.). Hybridized filters were washed for 1 hr at 37° C. in 2×SSC/0.1% SDS and exposed to Kodak X-OMAT AR film overnight. The EcoRI phage inserts from isolates 102, 108 and 109 were subcloned into the EcoRI site of pBluescript KS(+) (Stratagene) or subcloned directly into the EcoRI site of pBR322 derived from the *E. coli* strain Y1088 (Chiu et al., 1992, Cloning of complementary DNA inserts from phage DNA directly into plasmid vector. *Methods Enzymol.* 216:508–516) for DNA sequence analysis. One of the two EcoRI sites of phage clone 110 was missing and the insert cDNA could not be excised by EcoRI digestion. Therefore, primers flanking the phage EcoRI cloning site were used in polymerase chain reactions (PCR) to amplify the phage insert. A single band was isolated and cloned into the HindIII site of pBluescript KS(+). Rescreening of the cDNA library was carried out under high stringency using the 240 bp EcoRI-BamHI fragment of Clone 109 as a probe. Nested deletions of the phage clones 102, 109, 110 and 310 were generated in both orientations using the method of Henikoff, 1984, Unidirectional digestion with exonuclease III creates targeted breakpoints for DNA sequencing. *Gene* 28:351–359).

Double and single-stranded DNA from selected clones were sequenced using the dideoxy method (Sanger, 1977, DNA sequencing with chain-terminating inhibitors. *Proc. Natl. Acad. Sci. USA* 74:5463–5467) and Sequenase (USB).

RNA Isolation and Northern Hybridization

RNA was isolated from frozen tissues by acid guanidinium isothiocyanate extraction followed by CsCl gradient centrifugation (Chirgwin et al., 1979, Isolation of biologically active ribonucleic acid from sources enriched in ribonucleases. *Biochemistry* 18:5294–5299. RNA samples were electrophoresed through 1.0% agarose/formamide gels, transferred to Hybond-N nylon membranes and probed with anti-sense [$\alpha$-$^{32}$p]UTP-labled riboprobes. The filters were washed twice in 2×SSC/0.1% SDS for 15 min at 65° C. and twice in 0.1×SSC/0.1% SDS for 15 min at 65° C. The membranes were then exposed to Kodak X-OMAT AR film and developed.

In Situ Hybridizations

To generate FGFR2 specific riboprobes, a 306 bp BbsI-BamHI fragment from Clone 310 was subcloned into the SmaI site of pBluescript SK(+) and designated MP70-1. To generate an anti-sense transcript, 1 µg of MP70-1 was digested with EcoRI and in vitro transcription was carried out using T3 RNA polymerase according to the manufacturer's protocol (Stratagene). The sense strand transcript was generated by digestion of MP70-1 with BamHI followed by in vitro transcription using T7 RNA polymerase. FGFR1 specific riboprobes were generated using the exonuclease III/mung bean nuclease generated deletion clones used in the sequencing reactions (see above) that allowed the synthesis of the sense and anti-sense transcripts representing the 73 amino acid carboxy terminal tail of the receptor and 80 nucleotides of the 3'-untranslated sequence. All transcription reactions were performed in the presence of [$^{35}$S]UTPαS. The RNA probes were purified by Nuctrap push columns (Stratagene).

Blastemas with a small amount of stump tissue were isolated and fixed in 4% paraformaldahyde containing 1×PBS, pH 7.2, for 2 hr at 4° C. The blastemas were then washed two times in 1×PBS at 4° C. for 30 min, and frozen on a dry ice/isopropanol slurry in OCT compound. Ten/µm cryosections were placed on TESPA (3-triethoxysilylpropylamine) treated slides and fixed for 20 min in 4% paraformaldehyde containing 1×PBS. The slides were dehydrated through graded ethanol and stored at −80° C. until hydridization. Prior to hybridization the sections were treated with proteinase K (20 µg/ml) for 10 min at 37° C., acetylated by immersing slides in 0.25% acetic anhydride in 0.1M triethanolamine buffer, pH 8.0 for 20 min and dehydrated through graded ethanol solutions. The hybridizations were carried out at 50°–55° C. in hybridization mix (50% formamide, 0.3M NaCl, 10 mM Tris-HCl, 1×Denhardt's solution, 5 mM EDTA, 0.5 mg/ml yeast tRNA, 10% dextran sulfate, pH 7.5) with either sense or antisense riboprobes at a concentration of $1\times10^7$ cpm/ml for 16 hr.

Slides were washed in 4X SSc for 5 min at room temperature before a 30 min wash in 50% formamide/2X SSC/0.1% 2-mercaptoethanol at 50°–55° C. The slides were then treated with RNase A (20μg/ml) for 30 min at 37° C. The slides were further washed in 50% formamide/2×SSC/ 0.1% 2-mercaptoethanol for 30 min at 50°–55° C., 2X and 0.1X SSC each for 15 min at 50°–55° C. The sections were then dehydrated, coated with Kodak NTB-2 emulsion diluted 1:1 with distilled water and exposed for 15 to 20 days. Slides were developed with Kodak D-19 developer for 2.5 min at 15° C. and fixed for 5 min with Kodak fixer. Sections were stained with hematoxylin and counterstained with eosin. The sections were visualized with both dark- and light-field microscopy.

The newt aFGF proteins are useful biological materials for promoting in vitro growth of cultured cell lines, such as cell lines that have been transformed by recombinant DNA techniques to produce other useful proteins. The aFGF proteins are also useful for enhanced would healing.

Substantially pure aFGF or the non-toxic salts thereof, can be combined with a pharmaceutically acceptable carrier to form a pharmaceutical composition and may be administered to mammals in an acceptable manner such as intravenously, subcutaneously, intramuscularly or orally. It is to be understood that the required dosage will vary with the particular condition being treated, with the severity of the condition and with the duration of desired treatment. For example, such peptides can be administered in the form of pharmaceutically acceptable non-toxic salts, (i.e., acid addition salts or metal complexes, e.g., with zinc, iron or the like, which are considered as salts for purposes of this application). It is known that acid addition salts include hydrochloride, hydrobromide, sulphate, phosphate, maleate, acetate, citrate, benzoate, succinate, malate, ascorbate, tartrate and the like. According to acceptable pharmaceutical practices if the active ingredient is administered in tablet form, the tablet may contain a binder, such as tragacanth, corn starch or gelatin; a disintegrating agent, such as alginic acid; and a lubricant, such as magnesium stearate. If the active ingredient is administered in liquid form, sweetening and/or flavoring may be used. If the active ingredient is administered by intravenous injection, the active ingredient maybe delivered in isotonic saline, phosphate buffer solutions or the like.

Further, according to acceptable pharmaceutical practices the active ingredient should be administered under the guidance of knowledgeable persons. The pharmaceutical compositions will usually contain the active ingredient in conjunction with a conventional, pharmaceutically-acceptable carrier. The aFGF active ingredients may be administered in conjunction with other therapeutic agents, including other mitogens, such as platelet-derived growth factor, epidermal growth factor, insulin-like growth factors, and transforming growth factors.

C. Biochemical and Functional Characterization of Newt FGFR2

To characterize the newt FGFR cDNA functionally, the newt KGFR were expressed in CHO-K1 cells. The mammalian expression vector, pBJ5, which contains a chimeric promoter derived from HTLV-I and SV40, was used to express the newt KGFR and FGFR2 cDNA. Crosslinking studies on CHO-K1 cells over-expressing the newt KGFR (KPTr2-2) showed a crosslinked product migrating at 150 kDa when using $^{125}$I-labeled bovine brain aFGF or recombinant human aFGF as the ligand. The crosslinked product can be successfully competed off with a 500-fold molar excess of cold aFGF or human recombinant KGF as shown in FIG. 11. The crosslinked product is absent in KPTr1-8, the CHO cells that were transfected with the pBJ5 vector alone. The crosslinked product thus appears to be specific. Similarly, a cell line over-expressing the human KGFR (T-1063-29-2 from S. A. Aaronson, NIH) was able to produce a somewhat smaller crosslinked product than the newt KGFR. Antibodies (both monoclonal and polyclonal) directed against a peptide from the carboxyl terminus of the newt FGFR2 are generated.

Binding assays using KPTr2-2 and $^{125}$I-aFGF have been carried out. The Scatchard plot from these assays revealed that the newt KGFR has a $K_d$ of 1.3 nM toward human aFGF and the KPTr2-2 cell line expresses about 355,500 receptors per cell. The $K_d$ is slightly higher than the typical sub-nM range of mammalian KGFR. However, this may reflect the species difference since we used a human ligand for the newt receptor. A competition assay using KPTr2-2 and $^{125}$I-aFGF showed that human recombinant bFGF does not compete as well as aFGF. This result is consistent with the observation published for human KGFR.

The CHO-K1 cell line (KPTr2-2) expressing newt KGFR has been deposited with the ATCC on May 25, 1993 and given Accession Number CRL-11361.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture.

The depositor acknowledges the duty to replace the deposit should be depository be unable to furnish a sample when requested, due to the condition of the deposit. All restrictions on the availability to the public of the subject culture deposit will be irrevocably removed upon the granting of a patent disclosing it.

D. Mutant Cell Lines that are Non-responsive to FGF

Cells transfected with the cDNA coding for the full-length human aFGF were compared with the parental NIH/3T3 cells by determining their responses to various mitogens. The sense transfectants (Tr31-5-1, Tr33-1-2, Tr34-4-1 and Tr34-1-1) displayed stronger mitogenic responses than NIH/3T3 cells when stimulated with calf serum or PDGF consistent with their being faster-growing cells. The sense transfectants, with the exception of Tr33-1-2, respond less strongly than the parental NIH/3T3 cells to the truncated form of aFGF (b-aFGF) and to the full-length aFGF (rh-1FGF) for which Tr31-5-1 is the source. In fact, Tr31-5-1 and Tr33-1-2 failed to give any mitogenic responses to the full-length aFGF as shown in FIG. 12. These results suggest that truncated aFGF may utilize a different signaling pathway from that of the full-length aFGF. Both Swiss/3T3 and NIH/3T3, as well as sense transfectants expressing low levels of full-length aFGF and anti-sense transfectants, responded to the mitogenic stimulation of rh-aFGF. Therefore, the lack of mitogenic response of Tr31-5-1and Tr33-1-2 to rh-aFGF is not likely due to the trivial explanation of a defective mitogen. Thus, Tr31-5-1 and Tr33-1-2 may have lost some component of the pathway and these cell lines provide a unique means for elucidating the components responsive to the full-length aFGF.

Cell lines transfected with bFGF cDNA, which over-express bFGF, down-regulate its cognate receptor. Cell lines over-expressing full-length aFGF down-regulate its cognate receptor which is different from that used by the truncated aFGF and vice versa. Therefore, the reduction in mitogenic response of Tr31-5-1 and Tr33-1-2to full length aFGF is a consequence of fewer cell-surface ligand binding sites. The inventors' crosslinking data using $I^{125}$-labeled b-aFGF show that Tr31-5-1 cells have 50% less cell-surface binding to truncated aFGF than NIH/3T3 cells. These cell lines are useful for the identification of agonists and antagonists of aFGF and other FGF proteins.

Since aFGF elicits its profound responses in cells through interactions with membrane FGFR, it is important to identify domains in both the ligand and the receptors that interact with each other. These results are essential to understand the molecular basis of the multiple functions of FGF action in physiological and pathological conditions. This understanding provides the basis for the rational design of both ligand and receptor antagonists. Availability of cDNA coding for aFGF and four different aFGF receptors from the same amphibian species provides reagents useful for performing "mix and match" experiments between the human and newt receptor cDNAs, as well as between human and newt aFGF cDNAs, such that antagonists and agonists to the receptors as derivatives of human or newt aFGF are thus identified.

Although the invention has been described with regard to its preferred embodiments, which constitute the best mode presently known to the inventors, it should be understood that various changes and modifications, as would be obvious to one having the ordinary skill in this art, may be made without departing from the scope of the invention which is set forth in the claims appended hereto.

We claim:

1. A cDNA clone comprising a DNA sequence coding *Notophthalmus viridescens* acidic fibroblast growth factor (aFGF) as shown in Sequence ID No. 2.

2. A cDNA clone of claim 1 wherein the cDNA is as shown in Sequence ID No. 1.

3. An isolated DNA clone comprising a DNA sequence encoding *Notophthalmus viridescens* acidic fibroblast growth factor including an initiation codon positioned upstream and adjacent the codon encoding the $NH_2$ terminal amino acid of naturally occurring *Notophthalmus viridescens* acidic fibroblast growth factor.

4. A recombinant host microorganism containing a DNA expression vector comprising a DNA sequence encoding *Notophthalmus viridescens* acidic fibroblast growth factor, wherein the microorganism is capable of expressing said factor.

5. An isolated DNA clone encoding *Notophthalmus viridescens* acidic fibroblast growth factor protein comprising an initiation codon positioned upstream and adjacent an open reading frame comprising a DNA sequence encoding *Notophthalmus viridescens* acidic fibroblast growth factor.

6. An isolated DNA clone according to claim 5, wherein the 5'-terminus of said open reading frame begins with a DNA sequence 5'-TTY ACA GCN CTG ACN GAR AAR TTY AA-3' as shown in Sequence ID No 11.

7. A vector comprising the DNA clone according to claim 6.

8. A recombinant host microorganism containing a plasmid comprising the DNA clone according to claim 6.

9. A replicable DNA expression vector capable of expressing the DNA clone according to claim 6 in a self-replicating recombinant host.

10. An isolated DNA clone according to claim 5, wherein the 5'-terminus of the anti-sense strand of said open reading frame begins with a DNA sequence 5'-TAG GTR TTR TAR TGR TTY TCY TC-3' as shown in Sequence ID No. 12.

11. A vector comprising the DNA clone according to claim 10.

12. A recombinant host microorganism containing a plasmid comprising the DNA clone according to claim 10.

13. A vector comprising the DNA clone according to claim 5.

14. A recombinant host microorganism containing a plasmid comprising the DNA clone according to claim 5.

15. A replicable DNA expression vector capable of expressing the DNA clone according to claim 5 in a self-replicating recombinant host.

16. A recombinant host transformed with the vector of claim 15.

17. The recombinant host according to claim 16, wherein said host is in a cell.

18. The recombinant host according to claim 16 obtained by transforming or infecting a member of the group consisting of the *E. coli, B. subtillis*, insect, yeast and vertebrate cell with the replicable DNA expression vector.

19. The recombinant host according to claim 16 which is eukaryotic.

20. A process for producing a purified newt acidic fibroblast protein comprising maintaining a recombinant host microorganism, which includes a plasmid capable of expressing the open reading frame of the DNA sequence according to claim 5, under conditions such that the microorganism produces the protein, and isolating the protein.

* * * * *